US012733892B2

(12) United States Patent
Tajima

(10) Patent No.: US 12,733,892 B2
(45) Date of Patent: Sep. 15, 2026

(54) MAMMOGRAPHY APPARATUS

(71) Applicant: FUJIFILM Corporation, Tokyo (JP)

(72) Inventor: Takashi Tajima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 145 days.

(21) Appl. No.: 18/815,128

(22) Filed: Aug. 26, 2024

(65) Prior Publication Data

US 2025/0090117 A1 Mar. 20, 2025

(30) Foreign Application Priority Data

Sep. 20, 2023 (JP) ................................ 2023-153479

(51) Int. Cl.

| | |
|---|---|
| ***A61B 6/50*** | (2024.01) |
| ***A61B 6/00*** | (2024.01) |
| ***A61B 6/02*** | (2006.01) |
| ***A61B 6/04*** | (2006.01) |
| ***A61B 6/06*** | (2006.01) |
| ***A61B 6/40*** | (2024.01) |
| ***A61B 6/42*** | (2024.01) |

(52) U.S. Cl.

CPC .............. *A61B 6/502* (2013.01); *A61B 6/025* (2013.01); *A61B 6/0414* (2013.01); *A61B 6/0435* (2013.01); *A61B 6/06* (2013.01); *A61B 6/4035* (2013.01); *A61B 6/4291* (2013.01); *A61B 6/482* (2013.01); *A61B 6/484* (2013.01)

(58) Field of Classification Search

CPC ....... A61B 6/502; A61B 6/025; A61B 6/0414; A61B 6/0435; A61B 6/06; A61B 6/4035; A61B 6/4291; A61B 6/482; A61B 6/484

See application file for complete search history.

(56) References Cited

U.S. PATENT DOCUMENTS

| | | | | |
|---|---|---|---|---|
| 12,059,282 | B2 * | 8/2024 | He | A61B 6/502 |
| 2009/0003519 | A1 * | 1/2009 | Defreitas | A61B 6/502 378/37 |
| 2009/0041183 | A1 | 2/2009 | Yamakita | |
| 2016/0022230 | A1 | 1/2016 | Farbizio et al. | |
| 2018/0220980 | A1 | 8/2018 | Farbizio et al. | |
| 2019/0313989 | A1 | 10/2019 | Farbizio et al. | |

(Continued)

FOREIGN PATENT DOCUMENTS

| | | | | |
|---|---|---|---|---|
| JP | 2008-237631 A | | 10/2008 | |
| JP | 2012125364 A | * | 7/2012 | A61B 6/484 |
| JP | 2016-515877 A | | 6/2016 | |

*Primary Examiner* — Casey Bryant

(74) *Attorney, Agent, or Firm* — Studebaker Brackett PLLC

(57) ABSTRACT

A mammography apparatus includes an imaging table on which a breast of a subject is placed and in which a detector that detects radiation transmitted through the breast is housed, and a processor, in which a first grid and a second grid that are scattered ray removal grids, which are able to remove scattered rays generated by the radiation scattering in the breast, and that are switchable between an imaging position and a retreat position according to imaging in each of a plurality of imaging modes are provided inside the imaging table, and the processor is configured to acquire a result of receiving imaging mode selection of a user, and execute control of disposition states of the first grid and the second grid inside the imaging table according to the acquired imaging mode selection.

13 Claims, 16 Drawing Sheets

(56) References Cited

U.S. PATENT DOCUMENTS

| | | | | |
|---|---|---|---|---|
| 2020/0405248 | A1 | 12/2020 | Farbizio et al. | |
| 2022/0296187 | A1 | 9/2022 | Farbizio et al. | |
| 2023/0153969 | A1* | 5/2023 | Fukuda ................ | A61B 6/5217<br>382/130 |
| 2023/0404508 | A1 | 12/2023 | Farbizio et al. | |
| 2024/0206837 | A1* | 6/2024 | Tajima ................. | A61B 6/0414 |

* cited by examiner

FIG. 3

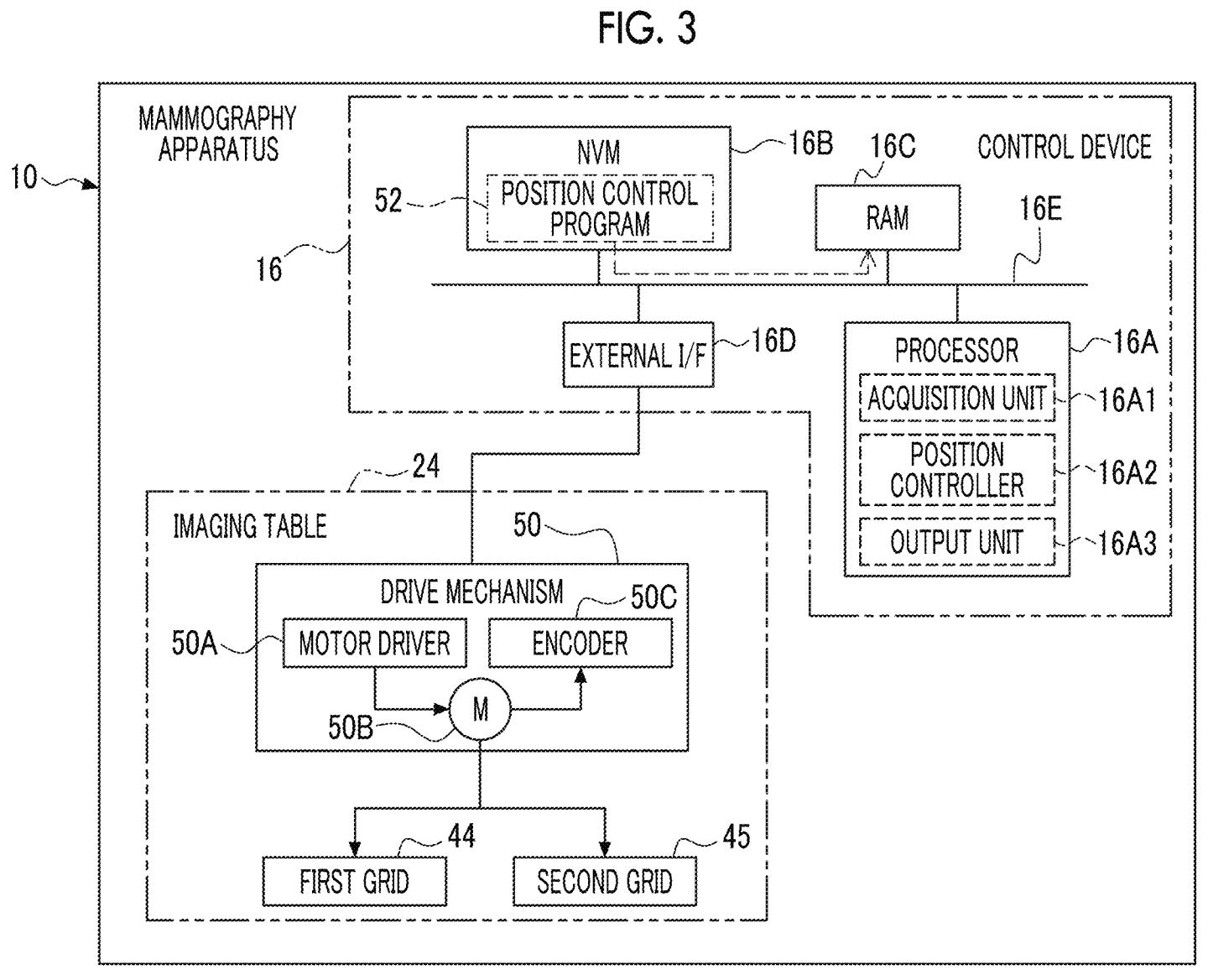

MAMMOGRAPHY APPARATUS
10
CONTROL DEVICE
16
16A
PROCESSOR
16A1
ACQUISITION UNIT
16A2
POSITION CONTROLLER
16A3
OUTPUT UNIT
16B
NVM
POSITION CONTROL PROGRAM
52
16C
RAM
16D
EXTERNAL I/F
16E
IMAGING TABLE
24
50
DRIVE MECHANISM
50A
MOTOR DRIVER
50B
M
50C
ENCODER
44
FIRST GRID
45
SECOND GRID

FIG. 11

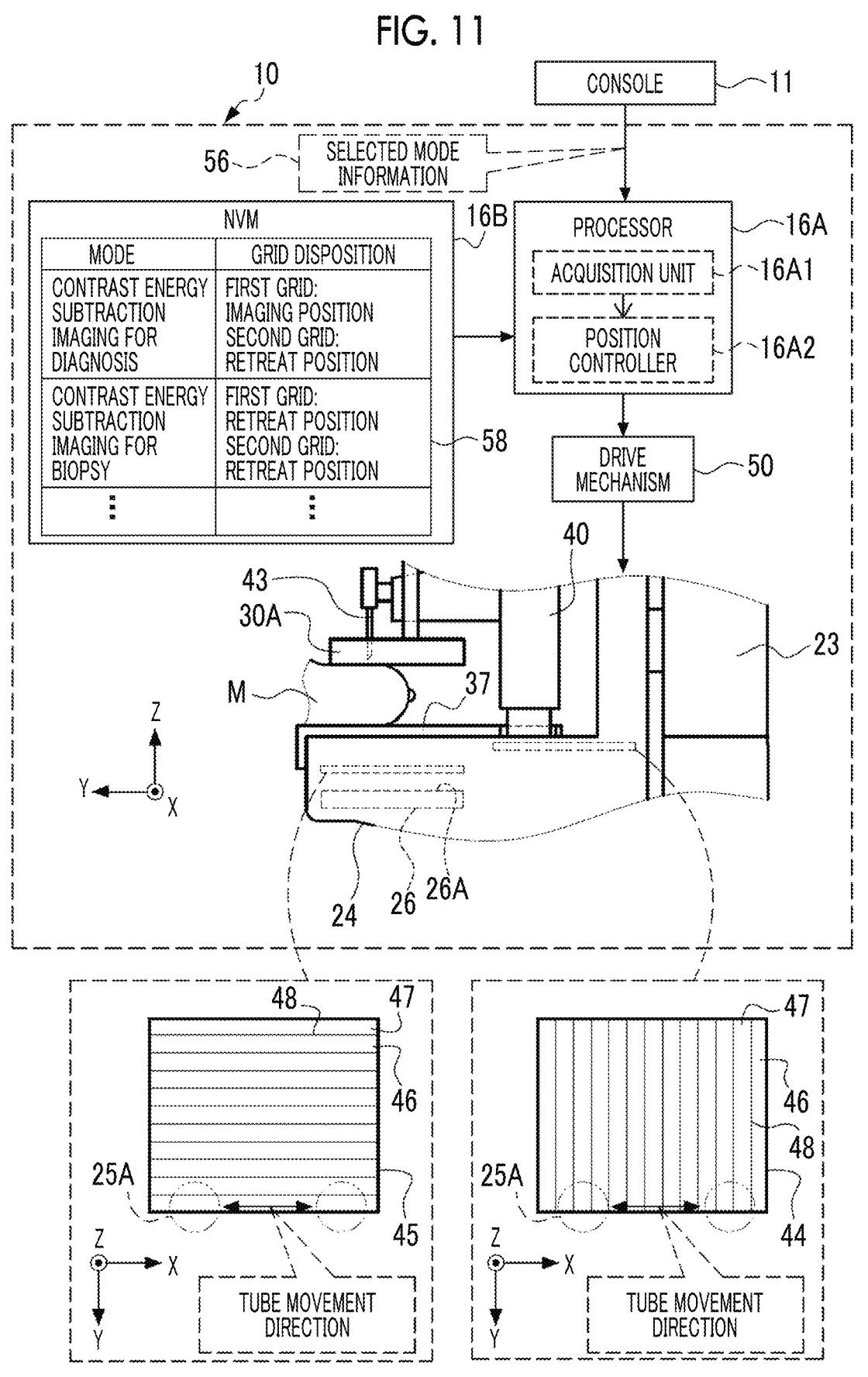

| MODE | GRID DISPOSITION |
|---|---|
| CONTRAST ENERGY SUBTRACTION IMAGING FOR DIAGNOSIS | FIRST GRID: IMAGING POSITION SECOND GRID: RETREAT POSITION |
| CONTRAST ENERGY SUBTRACTION IMAGING FOR BIOPSY | FIRST GRID: RETREAT POSITION SECOND GRID: RETREAT POSITION |
| ⋮ | ⋮ |

FIG. 15

| IMAGING MODE | USED GRID | DIRECTION OF BOUNDARY LINE OF GRID | DRIVE MECHANISM |
|---|---|---|---|
| NORMAL IMAGING | FIRST GRID | FRONT-REAR DIRECTION | FIRST GRID: IMAGING POSITION SECOND GRID: RETREAT POSITION |
| CONTRAST ENERGY SUBTRACTION IMAGING FOR DIAGNOSIS | FIRST GRID | FRONT-REAR DIRECTION | FIRST GRID: IMAGING POSITION SECOND GRID: RETREAT POSITION |
| CONTRAST ENERGY SUBTRACTION IMAGING FOR BIOPSY | SECOND GRID | LEFT-RIGHT DIRECTION (TUBE MOVEMENT DIRECTION) | FIRST GRID: RETREAT POSITION SECOND GRID: IMAGING POSITION |
| TOMOSYNTHESIS IMAGING | NONE | NONE | FIRST GRID: RETREAT POSITION SECOND GRID: RETREAT POSITION |

MAMMOGRAPHY APPARATUS

CROSS-REFERENCE TO RELATED APPLICATION

This application claims priority from Japanese Patent Application No. 2023-153479, filed on Sep. 20, 2023, the disclosure of which is incorporated by reference herein in its entirety.

BACKGROUND

Field of the Invention

The present disclosure relates to a mammography apparatus.

Related Art

JP2008-237631A describes a mammography apparatus that captures a radiation image of a breast by disposing a radiation transmission body and a radiation impermeable body that constitute a grid to extend to be substantially parallel to a chest wall of the breast, and irradiating a solid-state detector with radiation output from a radiation source through the grid.

JP2016-515877A describes an X-ray imaging device in which an anti-scattering grid having a plurality of partition walls can be configured to be positioned with respect to the X-ray imaging device such that each partition wall of the plurality of partition walls extends along a direction substantially parallel to a coronal plane of a target during imaging of the target using the X-ray imaging device. The X-ray imaging device can operate in a tomosynthesis imaging mode for imaging a chest of the target, and can include the anti-scattering grid that is disposed between a chest platform and an X-ray detector.

In the mammography apparatus, in addition to normal imaging, the breast may be imaged in a plurality of imaging modes, such as contrast energy subtraction imaging or tomosynthesis imaging. In this case, it is required to appropriately dispose scattered ray removal grids built in an imaging table according to the imaging mode.

SUMMARY

An object of the technology of the present disclosure is to provide a mammography apparatus that can realize disposition of an appropriate scattered ray removal grid according to an imaging mode.

A first aspect according to the technology of the present disclosure relates to a mammography apparatus comprising: an imaging table on which a breast of a subject is placed and in which a detector that detects radiation transmitted through the breast is housed; and a processor, in which a first grid and a second grid that are scattered ray removal grids, which are able to remove scattered rays generated by the radiation scattering in the breast, and that are switchable between an imaging position and a retreat position according to imaging in each of a plurality of imaging modes are provided inside the imaging table, and the processor is configured to acquire a result of receiving imaging mode selection of a user, and execute control of disposition states of the first grid and the second grid inside the imaging table according to the acquired imaging mode selection.

A second aspect according to the technology of the present disclosure relates to the mammography apparatus according to the first aspect, in which, in the scattered ray removal grid, a plurality of transmission parts that transmit the radiation and a plurality of absorption parts that absorb the radiation are alternately arranged, and a boundary line between the transmission part and the absorption part extends in one direction, and a direction in which the boundary line extends in the first grid and a direction in which the boundary line extends in the second grid intersect with each other.

A third aspect according to the technology of the present disclosure relates to the mammography apparatus according to the second aspect, in which, in the imaging table, in a case in which a direction connecting a chest wall side on which a chest wall of the subject is located and a side opposite to the chest wall is defined as a front-rear direction, and a direction orthogonal to the front-rear direction is defined as a left-right direction, the direction in which the boundary line extends in the first grid is parallel to the front-rear direction, and the direction in which the boundary line extends in the second grid is parallel to the left-right direction.

A fourth aspect according to the technology of the present disclosure relates to the mammography apparatus according to the third aspect, in which the plurality of imaging modes include a normal imaging mode in which the imaging is performed by holding a radiation source at a position facing the imaging table, and in a case in which the normal imaging mode is selected, the first grid is disposed at the imaging position, and the second grid is disposed at the retreat position.

A fifth aspect according to the technology of the present disclosure relates to the mammography apparatus according to the third aspect, in which the plurality of imaging modes include a first contrast imaging mode that is an imaging mode for diagnosis via contrast energy subtraction, and in a case in which the first contrast imaging mode is selected, the first grid is disposed at the imaging position, and the second grid is disposed at the retreat position.

A sixth aspect according to the technology of the present disclosure relates to the mammography apparatus according to the third aspect, in which the plurality of imaging modes include a second contrast imaging mode that is an imaging mode for biopsy via contrast energy subtraction, and in a case in which the second contrast imaging mode is selected, the second grid is disposed at the imaging position, and the first grid is disposed at the retreat position.

A seventh aspect according to the technology of the present disclosure relates to the mammography apparatus according to the third aspect, in which the plurality of imaging modes include a tomosynthesis imaging mode in which tomosynthesis of the breast is performed by moving a radiation source, and in a case in which the tomosynthesis imaging mode is selected, both the first grid and the second grid are disposed at the retreat position.

An eighth aspect according to the technology of the present disclosure relates to the mammography apparatus according to the fourth, sixth, and seventh aspects, in which the plurality of imaging modes include a continuous imaging mode in which at least any two of the normal imaging mode, the second contrast imaging mode, or the tomosynthesis imaging mode are continuously performed regardless of an order, and in the continuous imaging mode, the disposition states of the first grid and the second grid are changed according to each of the normal imaging mode, the second contrast imaging mode, and the tomosynthesis imaging mode.

A ninth aspect according to the technology of the present disclosure relates to the mammography apparatus according to the eighth aspect, in which, in the continuous imaging mode, the imaging in each mode in the continuous imaging mode is executable in a state in which the breast is being compressed between the imaging table and a compression plate.

A tenth aspect according to the technology of the present disclosure relates to the mammography apparatus according to the first aspect, in which, inside the imaging table, movement of the first grid and the second grid between the imaging position and the retreat position is linear movement.

An eleventh aspect according to the technology of the present disclosure relates to the mammography apparatus according to the first aspect, in which the processor is configured to output the disposition states of the first grid and the second grid inside the imaging table to a notification unit.

The object of the technology of the present disclosure provides the mammography apparatus that can realize disposition of an appropriate scattered ray removal grid according to the imaging mode.

BRIEF DESCRIPTION OF THE DRAWINGS

FIG. 3 is a diagram showing an example of an electrical system hardware configuration of the mammography apparatus.

FIG. 11 is a conceptual diagram showing an example of the function of the mammography apparatus.

FIG. 15 is a diagram summarizing a proper use of grids in the mammography apparatus.

DETAILED DESCRIPTION

Hereinafter, an embodiment of the present disclosure will be described in detail with reference to the drawings.

It should be noted that, in the following description, for convenience of description, a height direction, a width direction, and a front-rear direction (also referred to as a depth direction) of a mammography apparatus 10 are indicated by three arrows X, Y, and Z. First, the height direction is indicated by the arrow Z, an arrow Z direction indicated to by the arrow Z is an up direction of the mammography apparatus 10, and the opposite direction is a down direction. The height direction is a vertical direction. The width direction is indicated by the arrow X orthogonal to the arrow Z, a direction indicated by the arrow X is a right direction of the mammography apparatus 10, and the opposite direction is a left direction. The front-rear direction is indicated by the arrow Y as a direction orthogonal to the arrow Z and the arrow X, a direction indicated by the arrow Y is the front direction of the mammography apparatus 10, and the opposite is the rear direction. That is, in the mammography apparatus 10, a side of a stand 20 is the rear direction, and a side on which a subject A stands on the opposite side (see FIG. 2) is the front direction. In addition, in the following description, the expression using the side, such as an upper side, a lower side, a left side, a right side, a front side, and a rear side, has the same meaning as the expression using the direction.

In addition, in the present embodiment, "vertical direction" refers to the vertical direction in the sense of including an error generally allowed in the technical field to which the technology of the present disclosure belongs, that is, an error to the extent that it does not contradict the gist of the technology of the present disclosure, in addition to the exact vertical direction. In addition, similarly, "horizontal direction" refers to the horizontal direction in the sense of including an error generally allowed in the technical field to which the technology of the present disclosure belongs, that is, an error to the extent that it does not contradict the gist of the technology of the present disclosure, in addition to the exact horizontal direction.

Figure 1:
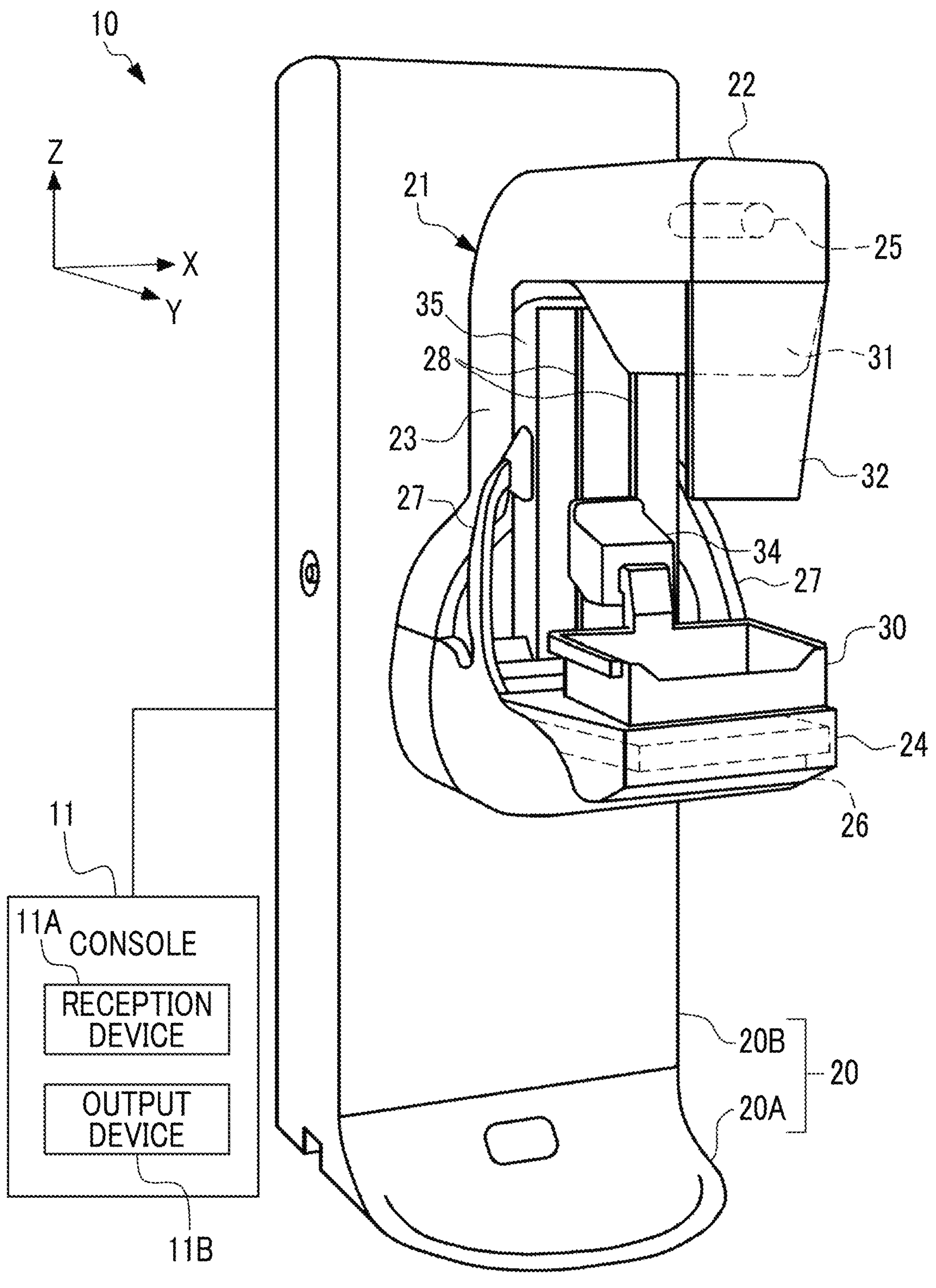
FIG. 1 is an exterior perspective view showing an example of a configuration of a mammography apparatus.
Figure 2:
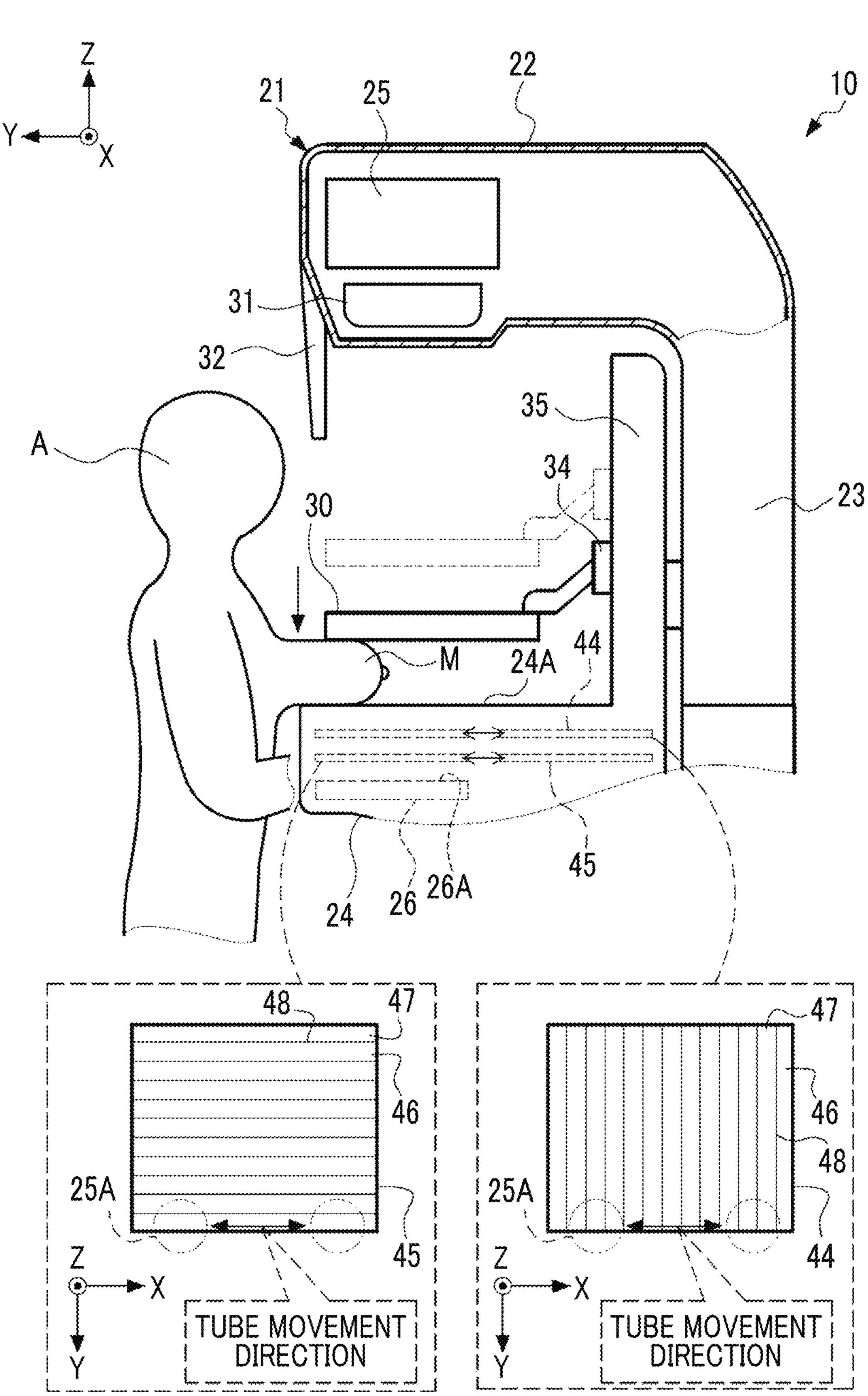
FIG. 2 is an exterior side view showing an example of the configuration of the mammography apparatus.

As shown in FIG. 1 and FIG. 2, the mammography apparatus 10 according to the present embodiment is a radiography apparatus that emits radiation toward a breast M of a subject A as a subject to obtain a radiation image of the breast M. The radiation is, for example, X-rays, but γ-rays may also be used. The subject A is located on a front side of the mammography apparatus 10. The mammography apparatus 10 is an example of a "mammography apparatus" according to the technology of the present disclosure.

The mammography apparatus 10 is connected to a console 11. The console 11 has a function of acquiring the radiation image captured by the mammography apparatus 10 and displaying the acquired radiation image, in addition to a setting function of setting the mammography apparatus 10 according to an imaging order. The console 11 is communicably connected to an image database server (not shown) via a network (not shown), such as a local area network (LAN).

The console 11 comprises a reception device 11A and an output device 11B. The reception device 11A receives input from a user. The reception device 11A is, for example, a keyboard and/or a mouse. The output device 11B displays an operation screen and/or an operation state of the mammography apparatus 10, a radiation image, or the like to the user. The output device 11B is, for example, a liquid crystal display or an organic electro luminescence (EL) display.

The mammography apparatus 10 is provided with a stand 20 and an arm 21. The stand 20 is configured by using a seat 20A installed on a floor of a radiography room and a support column 20B that extends in the height direction from the seat 20A. The arm 21 has a substantially C-shape as viewed from the left side, and is connected to the support column 20B via a rotation shaft. Since the arm 21 can be moved in the height direction with respect to the support column 20B, a height thereof can be adjusted according to a height of the subject A. In addition, the arm 21 can rotate about a rotation axis perpendicular to the support column 20B.

The arm 21 is configured by using a radiation source housing part 22, a body part 23, and an imaging table 24. A radiation source 25 is housed in the radiation source housing part 22. The radiation source 25 comprises a tube 25A. The radiation source housing part 22 has, for example, a housing structure having a longitudinal direction in the front-rear direction. The breast M of the subject A is placed on the imaging table 24. A radiation detector 26 is housed in the imaging table 24. The body part 23 integrally connects the radiation source housing part 22 and the imaging table 24. The body part 23 holds the radiation source housing part 22 and the imaging table 24 at predetermined positions. Handrails 27 for the subject A to grip are provided on both sides of the body part 23.

The breast M of the subject A is placed on the imaging table 24. The imaging table 24 comprises an imaging surface 24A on which the radiation transmitted through the breast M is incident. A radiation detector 26 is housed in the imaging table 24. The imaging table 24 is an example of an "imaging table" according to the technology of the present disclosure.

The radiation source 25 irradiates the breast M placed on the imaging table 24 with the radiation. The radiation emitted from the radiation source 25 is transmitted through a compression plate 30, and then incident on the breast M. The radiation detector 26 detects the radiation transmitted through the breast M, and outputs the radiation image. The radiation detector 26 is referred to as a flat panel detector (FPD). The radiation detector 26 may be an indirect conversion type that includes a scintillator converting the radiation into visible light and converts the visible light emitted from the scintillator into an electric signal, or may be a direct conversion type that directly converts the radiation into an electric signal. The radiation detector 26 is an example of a "detector" according to the technology of the present disclosure.

An irradiation field limiter 31 is provided between the radiation source 25 and the imaging table 24. The irradiation field limiter 31 is also referred to as a collimator, and defines an irradiation field of the radiation to the imaging table 24.

A face guard 32 is attached to the radiation source housing part 22. The face guard 32 is made or coated with a material that does not transmit the radiation, and protects a face of the subject A from the radiation.

The compression plate 30 that interposes and compresses the breast M with the imaging table 24 is provided between the imaging table 24 and the irradiation field limiter 31. The compression plate 30 is made of a material that transmits the radiation. The compression plate 30 is disposed at a position that faces the imaging table 24. In the present embodiment, the compression plate 30 is formed in a box shape with an open upper surface side.

A moving mechanism 35 supports the compression plate 30 to be movable between the radiation source 25 and the imaging table 24. In addition, the movable part 34 is disposed between the compression plate 30 and the moving mechanism 35. The movable part 34 is held by a rail 28 provided on the moving mechanism 35 to be movable slidingly. The rail 28 stretches in the up-down direction.

The moving mechanism 35 includes, for example, a motor (not shown), a motor driver (not shown), and a feed screw mechanism (not shown). The motor rotates according to an electric drive signal output by the motor driver, and moves the compression plate 30 via the feed screw mechanism.

The compression plate 30 is attached to the movable part 34. The movable part 34 is moved in the up-down direction together with the compression plate 30 by the moving mechanism 35. The up-down direction refers to, functionally, a direction in which the compression plate 30 is directed toward the imaging table 24 (that is, the down direction) and a direction in which the compression plate 30 is separated from the imaging table 24 (that is, the up direction). As described above, the compression plate 30 is configured to be movable in an aspect in which an interval with the imaging table 24 is changed.

A first grid 44 and a second grid 45 are provided inside the imaging table 24 as scattered ray removal grids. The scattered ray removal grid, as is well known, removes scattered rays generated by the radiation transmitting through the breast M. The first grid 44 and the second grid 45 are disposed inside the imaging table 24 on the radiation source 25 side with respect to the radiation detector 26. The first grid 44 and the second grid 45 are flat plate-shaped members, and comprise absorption parts 46 that absorb the radiation and transmission parts 47 that transmit the radiation. A boundary line 48 is formed between the absorption part 46 and the transmission part 47. The directions in which the boundary line 48 extends in the first grid 44 and the second grid 45 intersect with each other.

Specifically, in the first grid 44, the absorption parts 46 and the transmission parts 47 are alternately arranged, and the boundary line 48 between the absorption part 46 and the transmission part 47 is disposed inside the imaging table 24 in a state of extending in the front-rear direction (that is, a direction connecting a chest wall side of the subject A and an anti-chest wall side on the imaging surface 24A). Stated another way, the absorption parts 46 and the transmission parts 47 are alternately arranged in the left-right direction.

In the second grid 45, the absorption parts 46 and the transmission parts 47 are alternately arranged, and the boundary line 48 between the absorption parts 46 and the transmission parts 47 extends in the left-right direction. Stated another way, the absorption parts 46 and the transmission parts 47 are alternately arranged in the front-rear direction. As a result, in the second grid 45, the central axis of the flux of the radiation and an extending direction of the boundary line 48 substantially match, so that the occurrence of vignetting of the radiation is suppressed in the stereo imaging. The absorption part 46 is an example of an "absorption part" according to the technology of the present disclosure, and the transmission part 47 is an example of a "transmission part" according to the technology of the present disclosure. The boundary line 48 is an example of a "boundary line" according to the technology of the present disclosure. The first grid 44 is an example of a "first grid" according to the technology of the present disclosure. The second grid 45 is an example of a "second grid" according to the technology of the present disclosure.

Examples of a material of the absorption part 46 include a thin film of lead. In addition, examples of a material of the transmission part 47 include aluminum, paper, and carbon fiber.

Here, in the mammography apparatus 10 according to the present embodiment, the imaging in a plurality of imaging modes can be performed. The plurality of imaging modes include a normal imaging mode, a tomosynthesis imaging mode, a contrast energy subtraction imaging mode for diagnosis, and a contrast energy subtraction imaging mode for biopsy. One imaging mode is selected from among these imaging modes, and then the radiography is executed. Conditions of the imaging (for example, the presence or absence of movement of the radiation source 25, the presence or absence of the swing of the scattered ray removal grid, and the like) are different for each imaging mode. Therefore, it is required to change the disposition states of the scattered ray removal grids according to the imaging mode. Therefore, the first grid 44 and the second grid 45 can be switched between an imaging position and a retreat position according to the imaging in each of the plurality of imaging modes. Specifically, the first grid 44 and the second grid 45 are movable between the imaging position facing the detection surface 26A of the radiation detector 26 and the retreat position that is retracted from the imaging position in the imaging table 24.

As an example, as shown in FIG. 3, the mammography apparatus 10 comprises a control device 16. A drive mechanism 50 that moves the first grid 44 and the second grid 45 is provided inside the imaging table 24. The drive mechanism 50 moves the first grid 44 and the second grid 45 under the control of the control device 16.

The control device 16 comprises, for example, a processor 16A, a non-volatile memory (NVM) 16B, a random access memory (RAM) 16C, and an external interface (I/F) 16D. The processor 16A, the NVM 16B, the RAM 16C, and the external I/F 16D are electrically connected via a bus 16E. The processor 16A is an example of a "processor" according to the technology of the present disclosure.

The processor 16A is, for example, a central processing unit (CPU), and controls the respective units. In addition, the RAM 16C is a memory that temporarily stores information, and is used as a work memory by the processor 16A. The NVM 16B is a non-volatile storage device that stores various programs and various parameters. Examples of the NVM 16B include a flash memory (for example, an electrically erasable and programmable read only memory (EEPROM) and/or a solid state drive (SSD)). It should be noted that the flash memory is merely an example, and other non-volatile storage devices, such as a hard disk drive (HDD), may be employed or a combination of two kinds or more of non-volatile storage devices may be employed.

The external I/F 16D controls the transmission and reception of information between the control device 16 and the drive mechanism 50. The external I/F 16D outputs, for example, a signal for controlling the operation of the drive mechanism 50 to the drive mechanism 50.

The drive mechanism 50 includes a motor driver 50A, a motor 50B, and an encoder 50C. The motor driver 50A operates the motor 50B based on the signal output from the processor 16A via the external I/F 16D. The motor 50B rotates in response to the electric drive signal output by the motor driver 50A, and moves the first grid 44 and the second grid 45 via a power transmission mechanism (for example, a feed screw mechanism) (not shown). The encoder 50C converts a mechanical displacement amount of the rotation of the motor 50B into an electric signal and outputs the electric signal to the processor 16A.

As described above, the disposition of boundary line 48 is different between the first grid 44 and the second grid 45 provided inside the imaging table 24. Therefore, it is required that the first grid 44 and the second grid 45 are appropriately disposed according to the imaging mode.

Therefore, in view of such circumstances, in the mammography apparatus 10 according to the present embodiment, the processor 16A of the control device 16 reads out a position control program 52 from the NVM 16B, and executes the read out position control program 52 on the RAM 16C. As a result, the processor 16A operates as an acquisition unit 16A1, a position controller 16A2, and an output unit 16A3.

Figure 4:
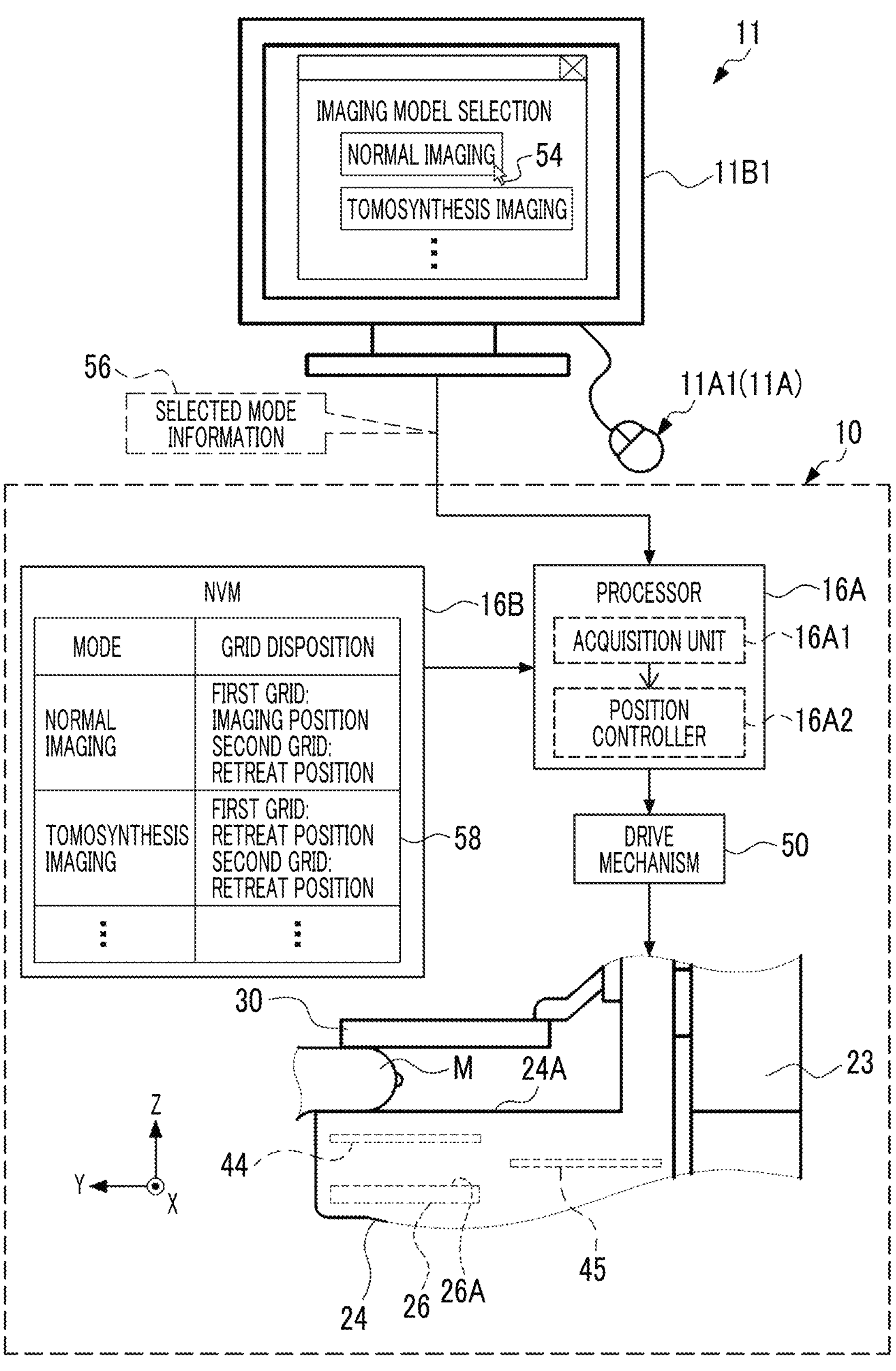
FIG. 4 is a conceptual diagram showing an example of a function of the mammography apparatus.

As shown in FIG. 4 as an example, first, in the console 11, the imaging mode selection of the user is received via the reception device 11A. In the example shown in FIG. 4, a mouse 11A1 as the reception device 11A is operated, so that the normal imaging mode is selected via a pointer 54 on an operation screen displayed on a display 11B1. In the normal imaging mode, the radiography is performed in a state in which the radiation source 25 is held at a position facing the imaging table 24. It should be noted that, here, as the imaging technique, the cranio-caudal (CC) imaging in which the breast M is compressed and imaged in the cranio-caudal direction of the subject is performed, but the medio-lateral (MLO) imaging in which the breast M is compressed and imaged in a direction inclined with respect to the cranio-caudal direction of the subject may be performed.

The console 11 outputs selected mode information 56, which is information indicating the imaging mode selected by the user, to the control device 16 of the mammography apparatus 10. That is, the console 11 outputs a result of receiving the imaging mode selection of the user.

In the processor 16A, the acquisition unit 16A1 acquires the selected mode information 56 from the console 11. That is, the acquisition unit 16A1 acquires the result of receiving the imaging mode selection of the user. In addition, the acquisition unit 16A1 acquires a grid position table 58 from the NVM 16B. The grid position table 58 is a table in which the imaging mode is input information and the grid disposition (that is, the positions of the first grid 44 and the second grid 45 in the imaging table 24) according to each imaging mode is output information. The acquisition unit 16A1 outputs the selected mode information 56 and the grid position table 58 to the position controller 16A2.

It should be noted that, here, although the form example is described in which the grid disposition is derived by the position controller 16A2 by using the grid position table 58, this is merely an example. A grid position calculation expression may be used instead of the grid position table 58. The grid position calculation expression is a calculation expression in which the imaging mode is an independent variable and the grid disposition according to each imaging mode is a dependent variable. The position controller 16A2 derives the grid disposition by using the grid position calculation expression.

The position controller 16A2 executes control of the disposition states of the first grid 44 and the second grid 45 inside the imaging table 24 according to the imaging mode selection of the user. Specifically, the position controller 16A2 derives the grid disposition according to the imaging mode indicated by the selected mode information 56 by using the grid position table 58. Then, the position controller 16A2 controls the drive mechanism 50 such that the derived grid disposition is realized. Specifically, the position controller 16A2 outputs a control signal for moving the first grid 44 and the second grid 45 to the derived grid disposition to the drive mechanism 50.

The drive mechanism 50 is operated under the control of the position controller 16A2 to move the first grid 44 and the second grid 45 to the grid disposition according to the imaging mode. In the example shown in FIG. 4, the normal imaging mode is selected by the user, so that the first grid 44 is disposed at the imaging position, and the second grid 45 is disposed at the retreat position. As described above, the position controller 16A2 executes the control of the disposition states of the first grid 44 and the second grid 45 inside the imaging table 24 according to the imaging mode selection of the user.

Figure 5:
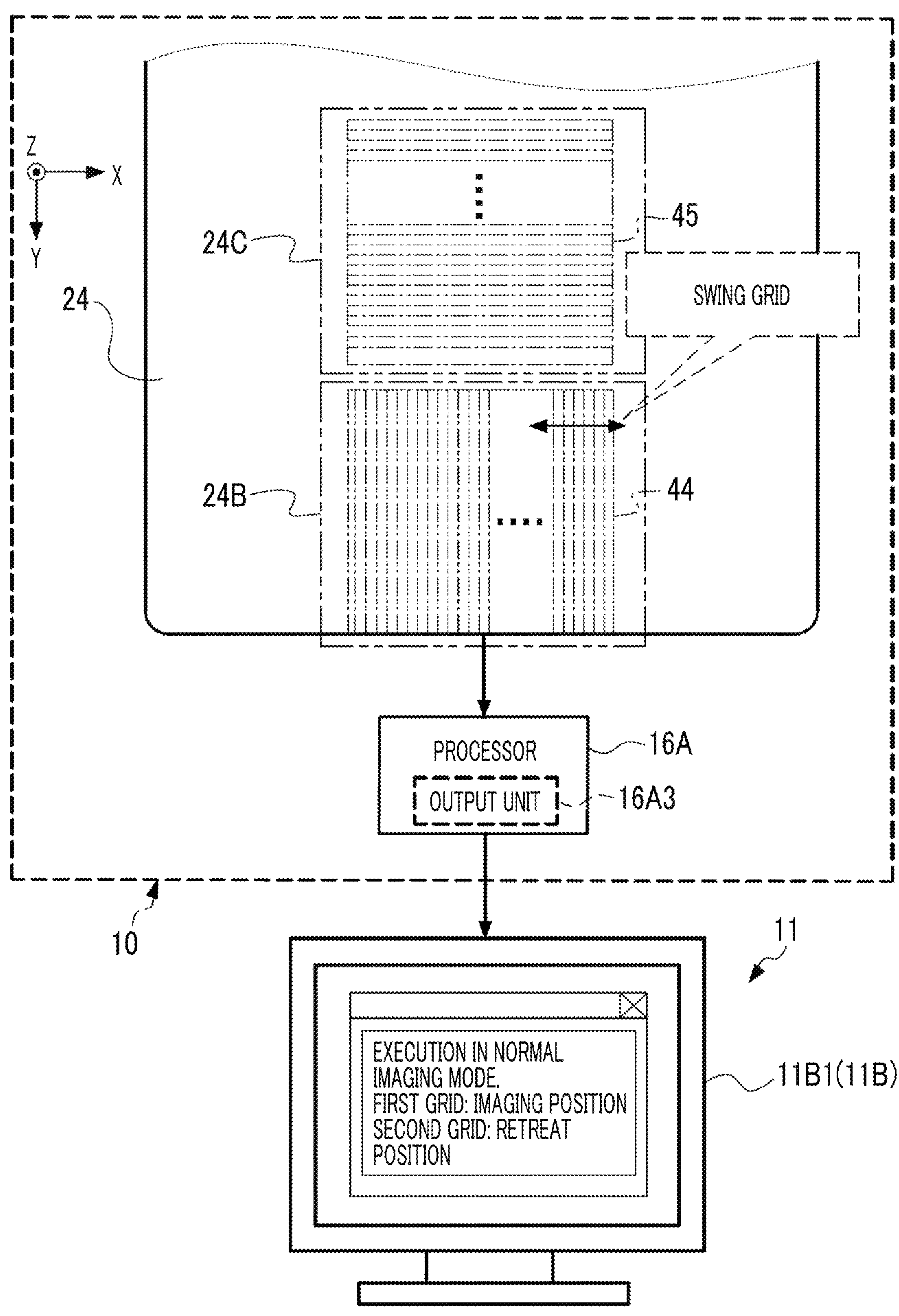
FIG. 5 is a conceptual diagram showing an example of the function of the mammography apparatus.

As shown in FIG. 5 as an example, as a result of the execution of the control of the disposition states of the first grid 44 and the second grid 45 via the position controller 16A2, the first grid 44 is disposed at the imaging position 24B, and the second grid 45 is disposed at the retreat position 24C. Here, the first grid 44 and the second grid 45 are linearly movable inside the imaging table 24. Here, inside the imaging table 24, the first grid 44 and the second grid 45 are linearly movable along the front-rear direction.

Then, in the processor 16A, the output unit 16A3 can output the information indicating the disposition states of the first grid 44 and the second grid 45 inside the imaging table 24. Specifically, the output unit 16A3 acquires information indicating the disposition states of the first grid 44 and the second grid 45, and outputs the acquired information to the console 11. In the console 11, the output device 11B displays the disposition states of the first grid 44 and the second grid 45. In the example shown in FIG. 5, a window including texts indicating the disposition states of the first grid 44 and the second grid 45 is displayed on the screen of the display 11B1. The output device 11B and the display 11B1 are examples of a "notification unit" according to the technology of the present disclosure.

It should be noted that, here, the form example is described in which the output device 11B is the display 11B1, but this is merely an example. The output device 11B may be a speaker and/or an indicator lamp in addition to or instead of the display 11B1.

The user starts the radiography of the breast M after confirming that the grid disposition is suitable for the selected imaging mode. In the example shown in FIG. 5, since the normal imaging mode is selected, the imaging is performed in a state in which the radiation source 25 is held at a position facing the imaging table 24. The first grid 44 is swung in the left-right direction during the imaging. As a result, the vignetting caused by the absorption part 46 can be removed.

Next, a case in which the contrast energy subtraction imaging mode for diagnosis is selected as the imaging mode will be described. The contrast energy subtraction imaging mode for diagnosis is an example of a "first contrast imaging mode" according to the technology of the present disclosure.

Figure 6:
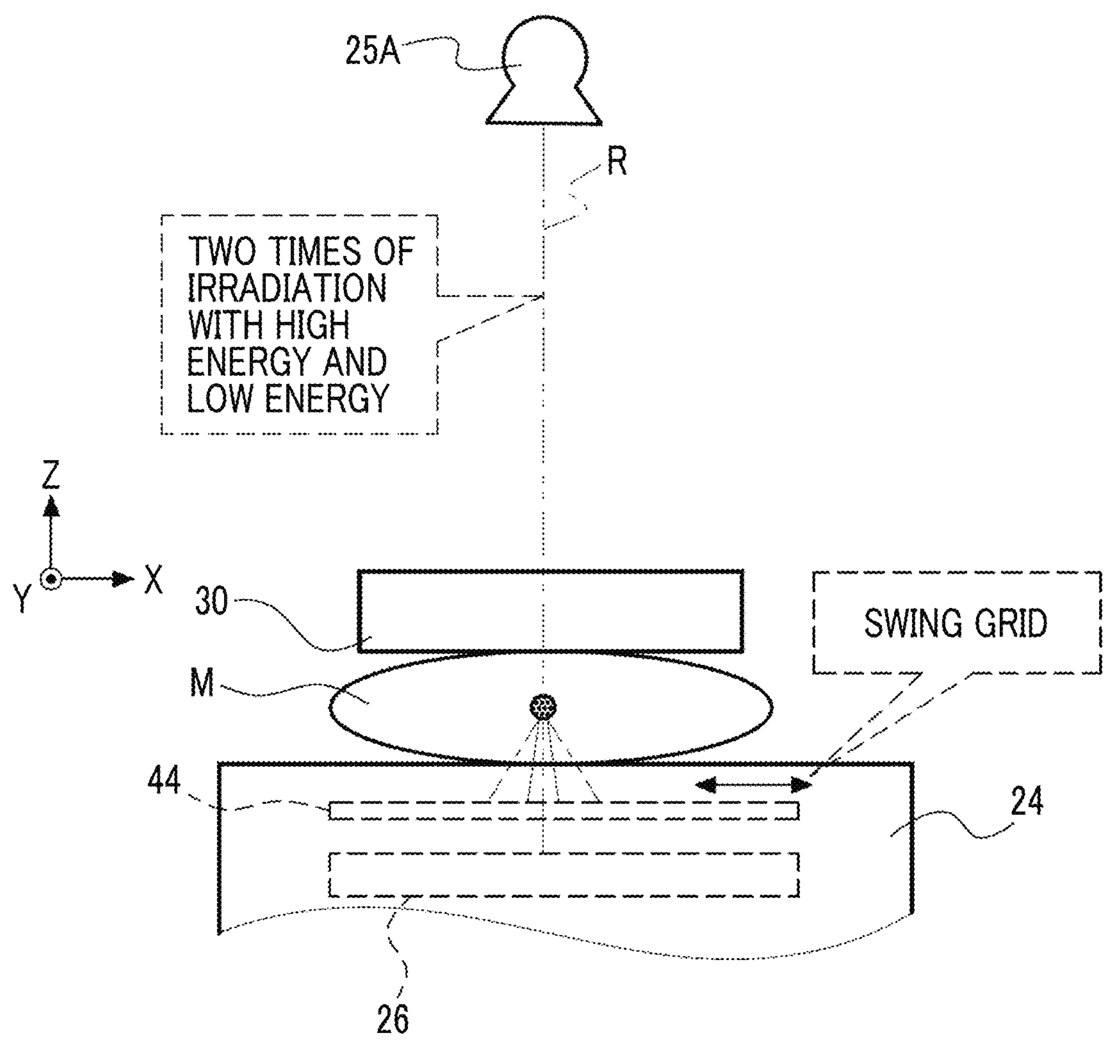
FIG. 6 is an exterior front view showing an example of the configuration of the mammography apparatus.

As an example, as shown in FIG. 6, the mammography apparatus 10 has a function of performing the contrast imaging. As a contrast agent used for the contrast imaging, a contrast agent using iodine having a k-absorption edge of 33 keV (hereinafter, simply referred to as a "contrast agent") is generally used. The mammography apparatus 10 uses the breast M to which the contrast agent is administered as the subject, captures a low-energy image by using the radiation detector 26 by emitting the radiation R having a first energy lower than the k-absorption edge of the contrast agent, and captures a high-energy image by using the radiation detector 26 by emitting the radiation R having a second energy higher than the k-absorption edge of the contrast agent. Specific first energy and second energy are determined from specifications of the mammography apparatus 10, a desired image quality of the radiation image, and exposure of the subject or the like in addition to the k-absorption edge of the contrast agent, and are generally preferably 22 keV to 49 keV.

The contrast agent and the tissue, such as a mammary gland, have different absorption characteristics of the radiation R. Therefore, in the high-energy image captured as described above, a body tissue, such as the mammary gland or fat, is shown, and the contrast agent is clearly shown. In addition, in the low-energy image, almost no contrast agent is shown, and the body tissue, such as the mammary gland, is clearly shown. Therefore, a difference image showing a difference between the low-energy image and the high-energy image can be made to be an image in which a mammary gland structure is removed and the contrast agent is clearly shown. This imaging is referred to as contrast energy subtraction imaging. Then, the diagnosis (for example, the determination of the presence or absence and the type of the lesion) is performed on the breast M by using the difference image obtained by the contrast energy subtraction imaging.

In the contrast energy subtraction imaging for diagnosis, the imaging is performed in a state in which the radiation source 25 is held at a position facing the imaging table 24 in the vertical direction in the same manner as in the normal imaging. In addition, the first grid 44 is swung in the left-right direction during the imaging. As a result, the vignetting caused by the absorption part 46 can be removed.

Figure 7:
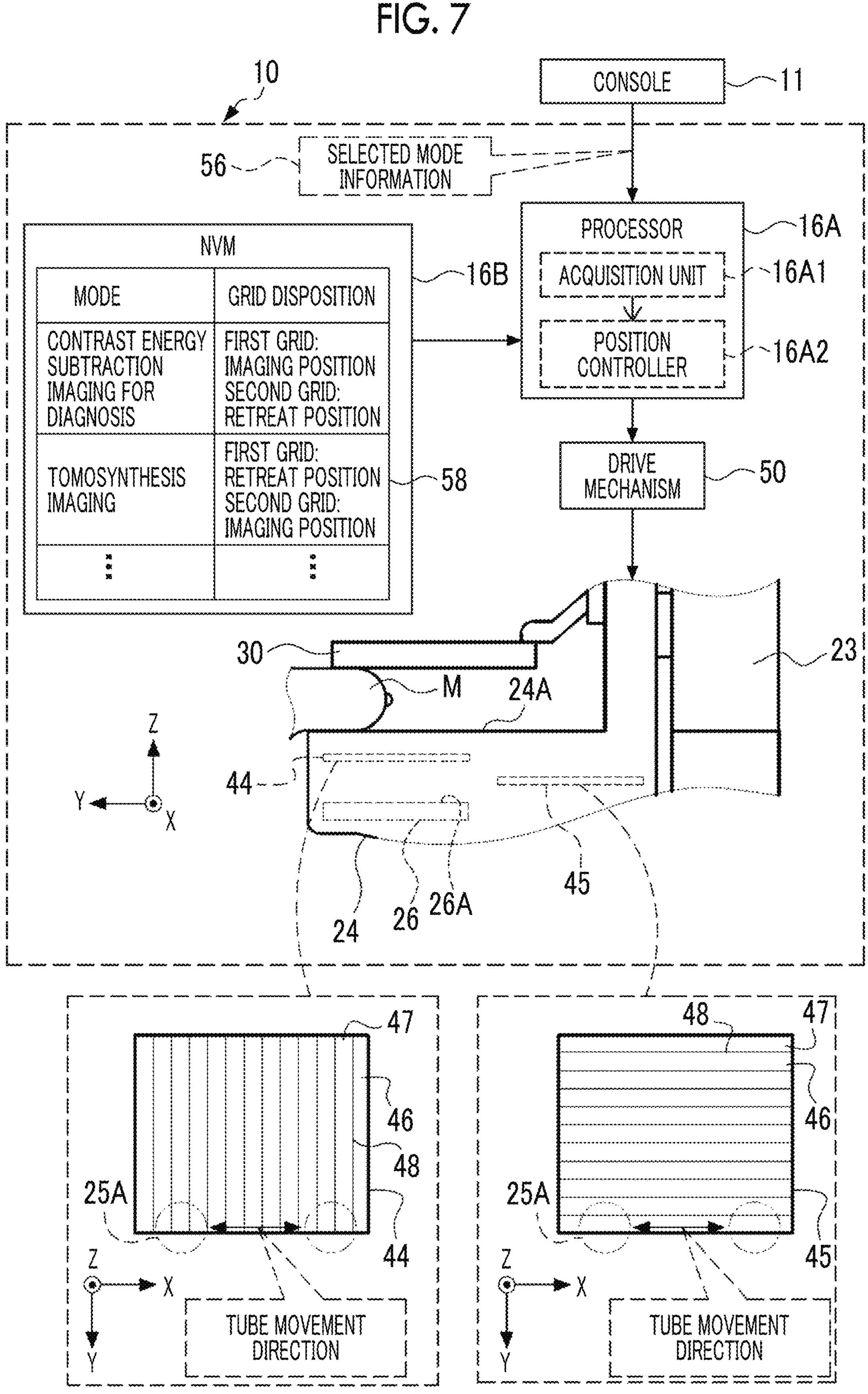
FIG. 7 is a conceptual diagram showing an example of the function of the mammography apparatus.

As an example, as shown in FIG. 7, the imaging mode selection of the user is received in the console 11. Here, the contrast energy subtraction imaging for diagnosis is selected. The console 11 outputs the selected mode information 56 to the mammography apparatus 10. That is, the console 11 outputs the result of receiving the imaging mode selection of the user.

In the processor 16A, the acquisition unit 16A1 acquires the selected mode information 56 from the console 11. In addition, the acquisition unit 16A1 acquires a grid position table 58 from the NVM 16B. The position controller 16A2 derives the grid disposition according to the imaging mode indicated by the selected mode information 56 by using the grid position table 58. Then, the position controller 16A2 controls the drive mechanism 50 such that the derived grid disposition is realized.

In the example shown in FIG. 7, since the contrast energy subtraction imaging mode for diagnosis is selected by the user, the first grid 44 is disposed at the imaging position, and the second grid 45 is disposed at the retreat position. As described above, the position controller 16A2 executes the control of the disposition states of the first grid 44 and the second grid 45 inside the imaging table 24 according to the imaging mode selection of the user.

Subsequently, a case in which the contrast energy subtraction imaging mode for biopsy is selected as the imaging mode will be described. The contrast energy subtraction imaging mode for biopsy is an example of a "second contrast imaging mode" according to the technology of the present disclosure. First, the biopsy unit 39 will be described as a premise of the contrast energy subtraction imaging for biopsy.

Figure 8:
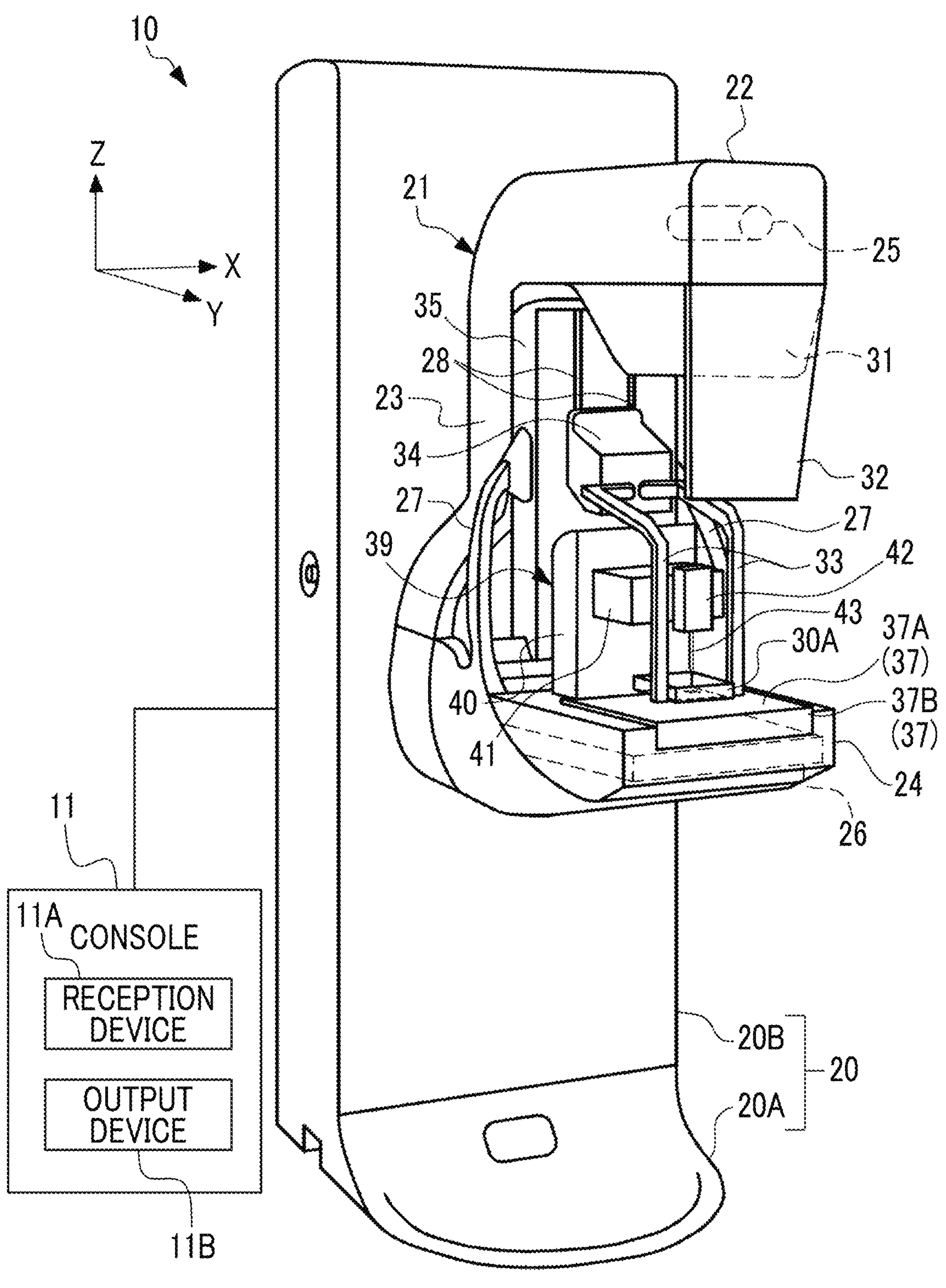
FIG. 8 is an exterior perspective view showing an example of the configuration of the mammography apparatus.
Figure 9:
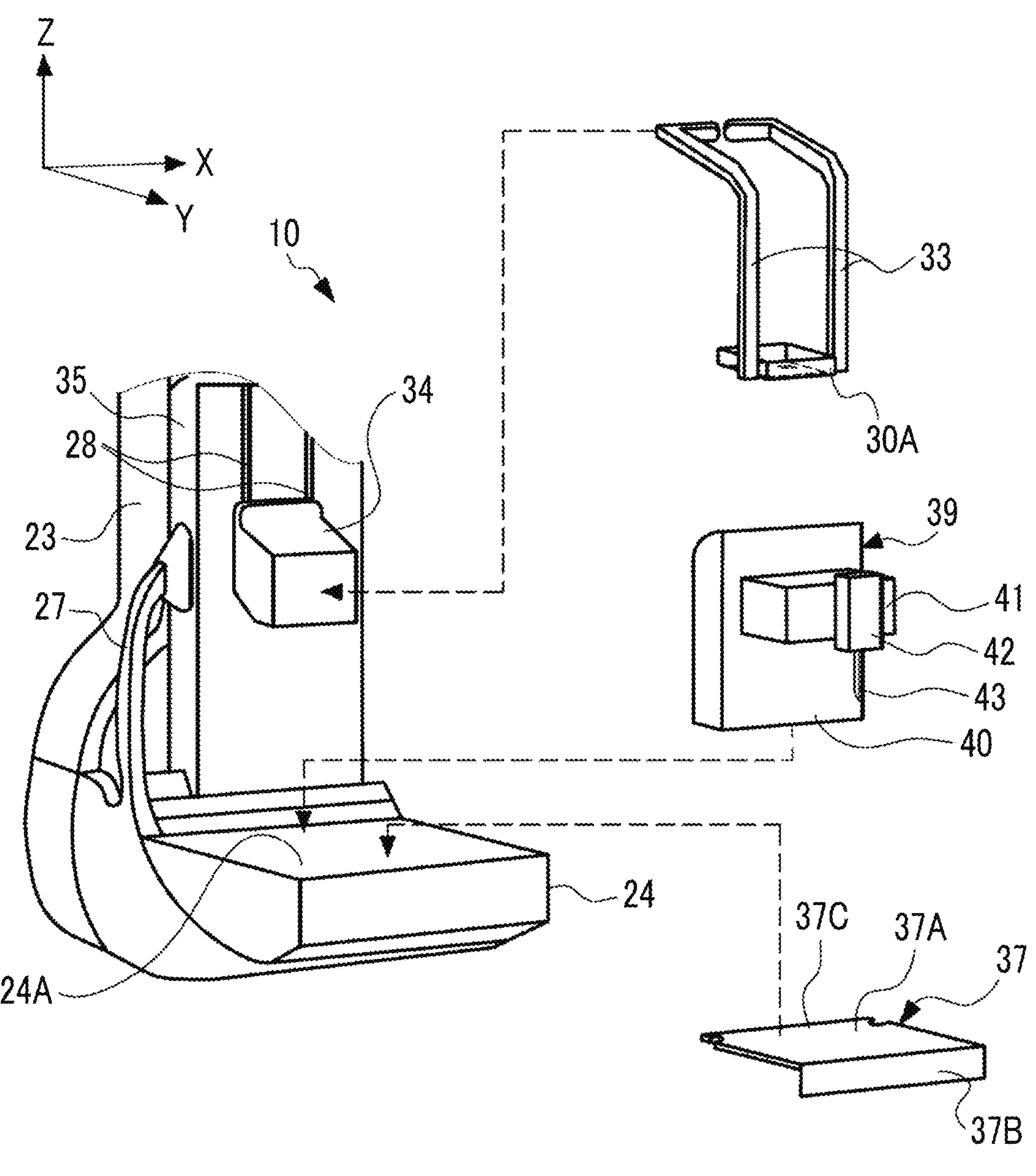
FIG. 9 is an exterior perspective view showing an example of a state in which a protective cover and a biopsy unit are attached to and detached from the mammography apparatus.

As an example, as shown in FIGS. 8 and 9, the biopsy unit 39 is attached to the mammography apparatus 10. The biopsy unit 39 is a unit that samples tissue in the breast M to perform a biological tissue sampling examination. The biopsy unit 39 comprises a body part 40, an adjustment part 41, a needle holding part 42, and a puncture needle 43. The adjustment part 41 can be moved with respect to the body part 40, and as a result, an insertion position, an insertion angle, and an insertion amount of the puncture needle 43 with respect to the breast M are adjusted. The needle holding part 42 holds the puncture needle 43. The puncture needle 43 has, for example, a double structure of an outer needle and an inner needle. As an example, a procedure for sampling the tissue with the puncture needle 43 is as follows. In a state in which the puncture needle 43 is inserted into the breast M and a tip end portion of the puncture needle 43 reaches a position of the tissue that is a sampling target, the inner needle protrudes from the outer needle to sample the tissue into a tissue sampling region formed on the inner needle. After sampling the tissue in the inner needle, the inner needle is housed in the outer needle, and the puncture needle 43 is pulled out from the breast M. As a result, the tissue that is the sampling target in the breast M is sampled. In addition, the compression plate 30A is provided with an opening on a bottom surface, and the puncture needle 43 is inserted into the breast M via the opening. The compression plate 30A is attached to the movable part 34 by a pair of support arms 33.

In a case in which a biopsy is performed by using the biopsy unit 39, a protective cover 37 is placed on the imaging table 24. The protective cover 37 protects the imaging surface 24A from the puncture needle 43. That is, the contact of the puncture needle 43 with the imaging surface 24A is suppressed by the protective cover 37. The protective cover 37 comprises a flat plate-shaped protective member 37A and an anterior wall 37B bent from a front end of the protective member 37A. The breast M is placed on the protective member 37A. The protective member 37A is made of a material that can transmit the radiation (for example, an acrylic resin). A size of the protective member 37A is a size in a range that can support the breast M, and a plate thickness of the protective member 37A has a strength that can support the breast M.

The biopsy unit 39 and the protective cover 37 are attached to the mammography apparatus 10 in a case in which the biopsy is performed. Stated another way, the biopsy unit 39 and the protective cover 37 are attachable to and detachable from the mammography apparatus 10. The protective cover 37 is attached to the imaging table 24 of the mammography apparatus 10 by utilizing, for example, magnetic attraction using a magnet. Specifically, the magnet is attached to the protective cover 37, and the magnet is magnetically attracted to a magnetizing plate provided on the imaging table 24 to attach the protective cover 37 to the imaging table 24. It should be noted that this is merely an example, and for example, the protective cover 37 may be attached to the imaging table 24 via a pressure-sensitive adhesive sheet, or the protective cover 37 may be attached to the imaging table 24 by fitting a part of the protective cover 37 into a recess provided in the imaging table 24.

The biopsy unit 39 is placed on the imaging table 24 after the protective cover 37 is attached to the imaging table 24. Specifically, the body part 40 of the biopsy unit 39 is placed above a rear end portion 37C of the protective cover 37. It should be noted that the biopsy unit 39 may be controlled to operate only in a case in which the protective cover 37 is attached to the imaging table 24.

In addition, the compression plate 30A is also a compression plate for the biopsy unit 39, and is attached to the mammography apparatus 10 by exchanging the compression plate 30 with the compression plate 30A for mammography in a case in which the biopsy is not performed.

Figure 10:
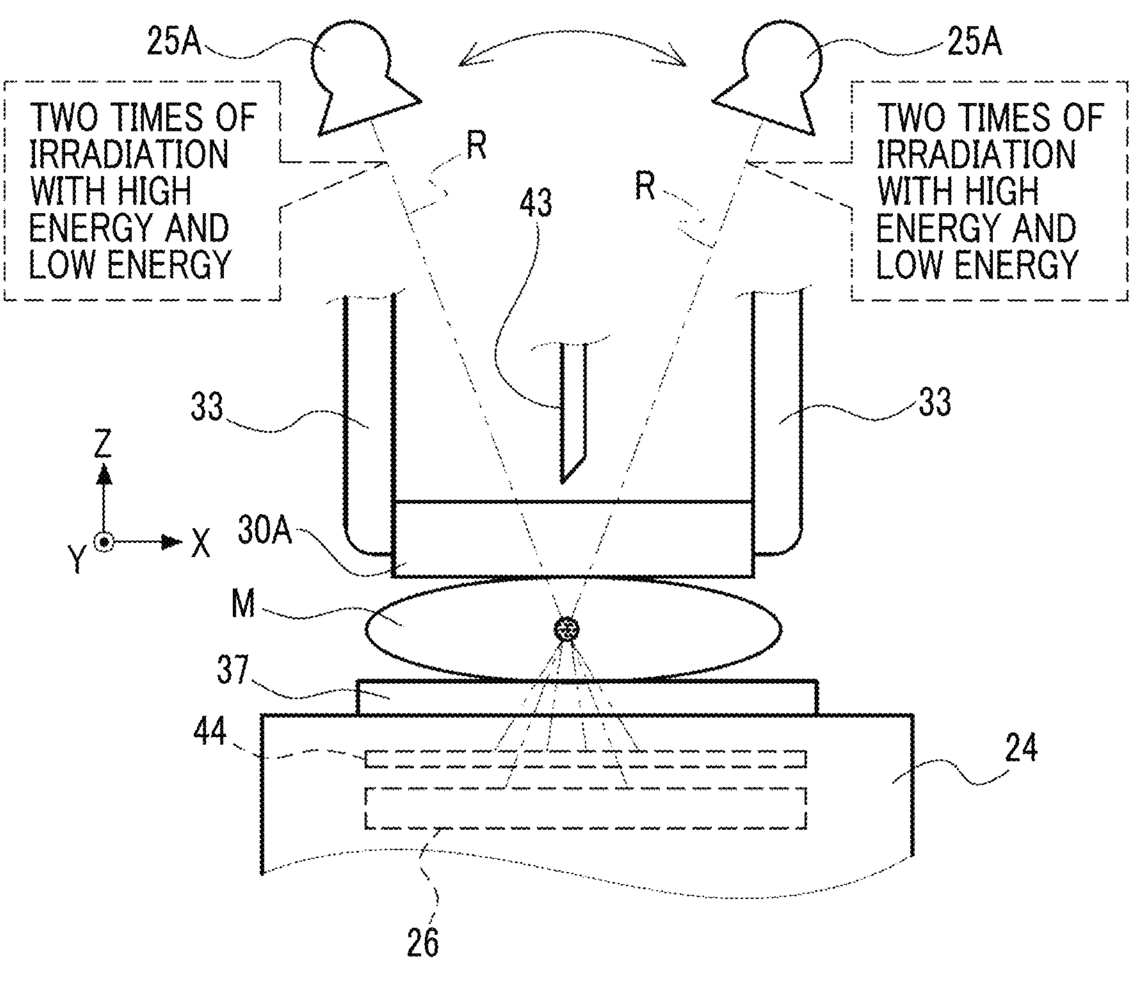
FIG. 10 is an exterior front view showing an example of the configuration of the mammography apparatus.

As shown in FIG. 10, for example, in a case in which the biopsy is performed, the puncture needle 43 is inserted into the breast M in a state in which the breast M is being compressed by the compression plate 30A. In such a case, it is required to accurately specify the position of the tissue (for example, a lesion tissue) that is the sampling target of the breast M. For this reason, as will be described below, in a case in which the biopsy is performed, in some cases, stereo imaging of emitting the radiation R toward the breast from two left and right directions having different irradiation angles with respect to the imaging table 24 is performed to three-dimensionally specify the position of the tissue that is the sampling target in the breast M.

In a case of the biopsy, the contrast energy subtraction imaging may be performed in order to three-dimensionally understand a position of a tissue that is a biopsy target in the breast M. In the stereo imaging, an irradiation position of the radiation R is changed in the left-right direction, so that the irradiation angle of the radiation R is changed and the imaging is performed a plurality of times. Then, the imaging with the radiation R having different energies (that is, the contrast energy subtraction imaging) is performed at each irradiation angle in the left-right direction in the stereo imaging. As a result, the tissue that is the biopsy target is clear in the image, and it is easier to understand the three-dimensional position. In this way, the contrast energy subtraction imaging for biopsy is performed by combining the stereo imaging and the contrast energy subtraction imaging.

As an example, as shown in FIG. 11, the imaging mode selection of the user is received in the console 11. Here, the contrast energy subtraction imaging for biopsy is selected. The console 11 outputs the selected mode information 56 to the mammography apparatus 10. That is, the console 11 outputs the result of receiving the imaging mode selection of the user.

In the processor 16A, the acquisition unit 16A1 acquires the selected mode information 56 from the console 11. In addition, the acquisition unit 16A1 acquires a grid position table 58 from the NVM 16B. The position controller 16A2 derives the grid disposition according to the imaging mode indicated by the selected mode information 56 by using the grid position table 58. Then, the position controller 16A2 controls the drive mechanism 50 such that the derived grid disposition is realized.

In the example shown in FIG. 11, since the contrast energy subtraction imaging mode for biopsy is selected by the user, the first grid 44 is disposed at the retreat position, and the second grid 45 is disposed at the imaging position. As described above, in the contrast energy subtraction imaging for biopsy, the stereo imaging is performed. In a case in which the stereo imaging is performed, in the mammography apparatus 10, the imaging is performed in a state in which the first grid 44 is moved to an anti-chest wall side (that is, a side of the body part 23) inside the imaging table 24. In the first grid 44, the boundary line 48 between the absorption part 46 and the transmission part 47 extends in a direction orthogonal to a movement direction of a tube 25A. Therefore, in a case in which the imaging is performed by moving the tube 25A by using the first grid 44, the central axis of the flux of the radiation and the boundary line 48 are orthogonal to each other, so that the vignetting of the radiation is more likely to occur. On the other hand, the second grid 45 has the boundary line 48 extending in a direction parallel to the movement direction of the tube 25A. Therefore, even in a case in which the imaging is performed by moving the tube 25A, the vignetting of the radiation is less likely to occur. Therefore, in the contrast energy subtraction imaging for biopsy, the first grid 44 is disposed at the retreat position, and the second grid 45 is disposed at the imaging position.

Figure 12:
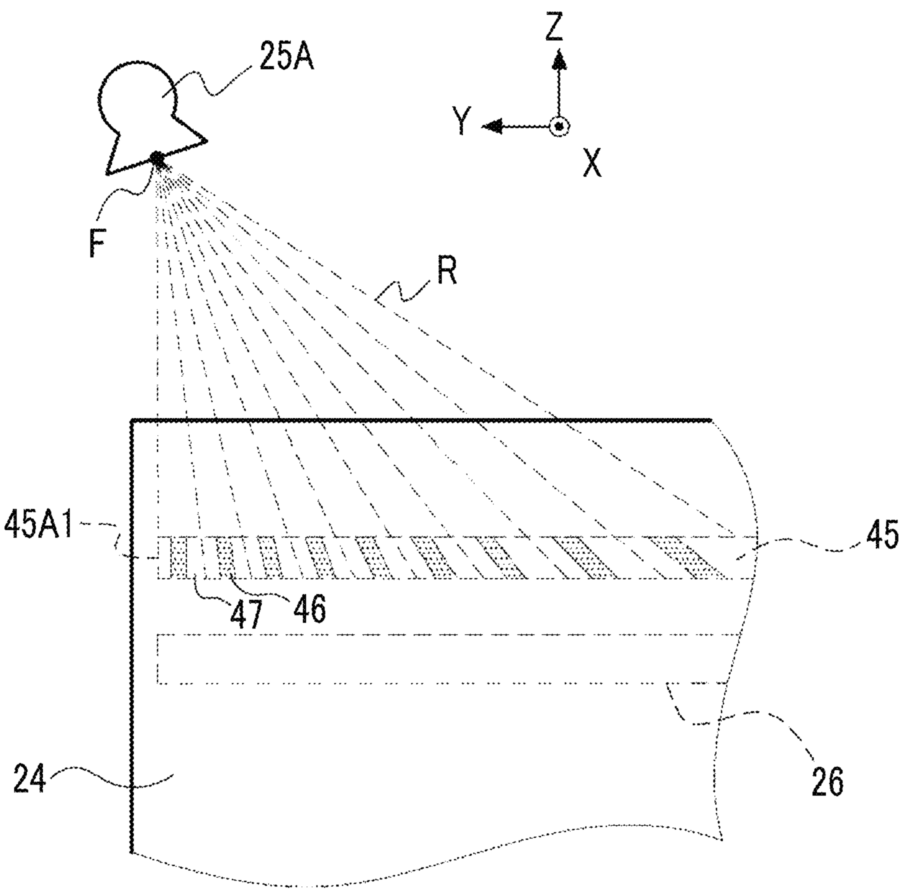
FIG. 12 is an exterior side view showing an example of the configuration of the mammography apparatus.

As shown in FIG. 12 as an example, the second grid 45 is a so-called focused grid. That is, in the second grid 45, a plurality of boundary surfaces of the absorption parts 46 and the transmission parts 47 are not parallel to each other, and a surface obtained by extending each of the plurality of boundary surfaces is inclined in an aspect in which the surface passes through a focal position F of the tube 25A and is focused on one straight line parallel to the boundary surface. In the present example, since the focal position F of the tube 25A is disposed on the side of the front end surface 45A1 of the second grid 45, inclination angles of the plurality of boundary surfaces are gradually increased from the front end surface 45A1 toward the rear side. By setting the second grid 45 as the focused grid, vignetting of the radiation R is further suppressed as compared with a parallel grid in which the plurality of boundary surfaces are parallel to each other.

Figure 13:
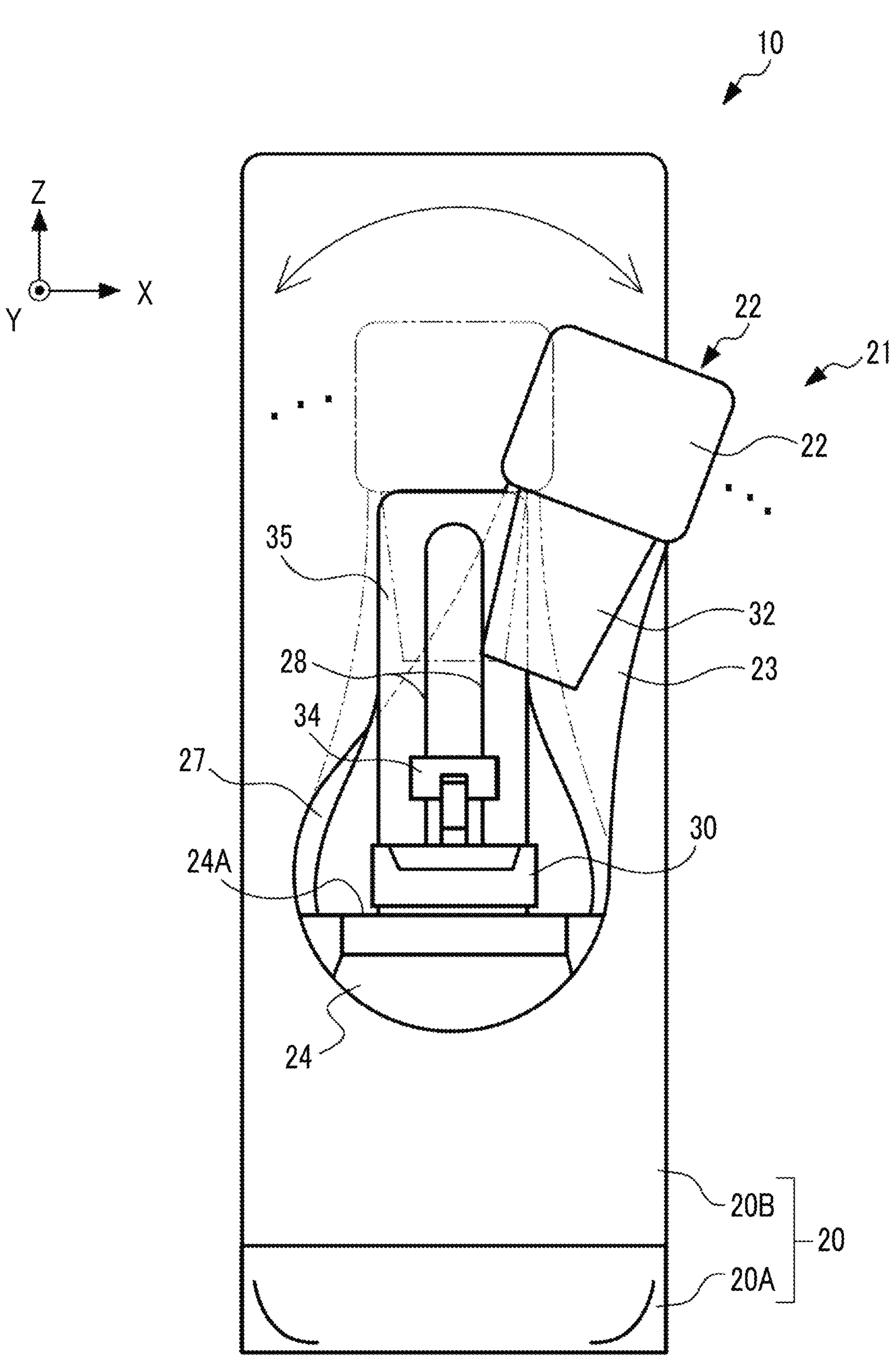
FIG. 13 is an exterior front view showing an example of the configuration of the mammography apparatus.

Subsequently, a case in which the tomosynthesis imaging mode is selected as the imaging mode will be described. As shown in FIG. 13 as an example, in the tomosynthesis imaging, the tomosynthesis of the breast M is performed by moving the radiation source. That is, in the tomosynthesis imaging, in order to obtain a tomographic image of the breast M, the breast M is imaged from a plurality of irradiation positions having different irradiation angles. Projection images of the breast M from the plurality of irradiation positions obtained by the tomosynthesis imaging are subjected to image reconstruction processing and used for generating the tomographic image of the breast M.

Figure 14:
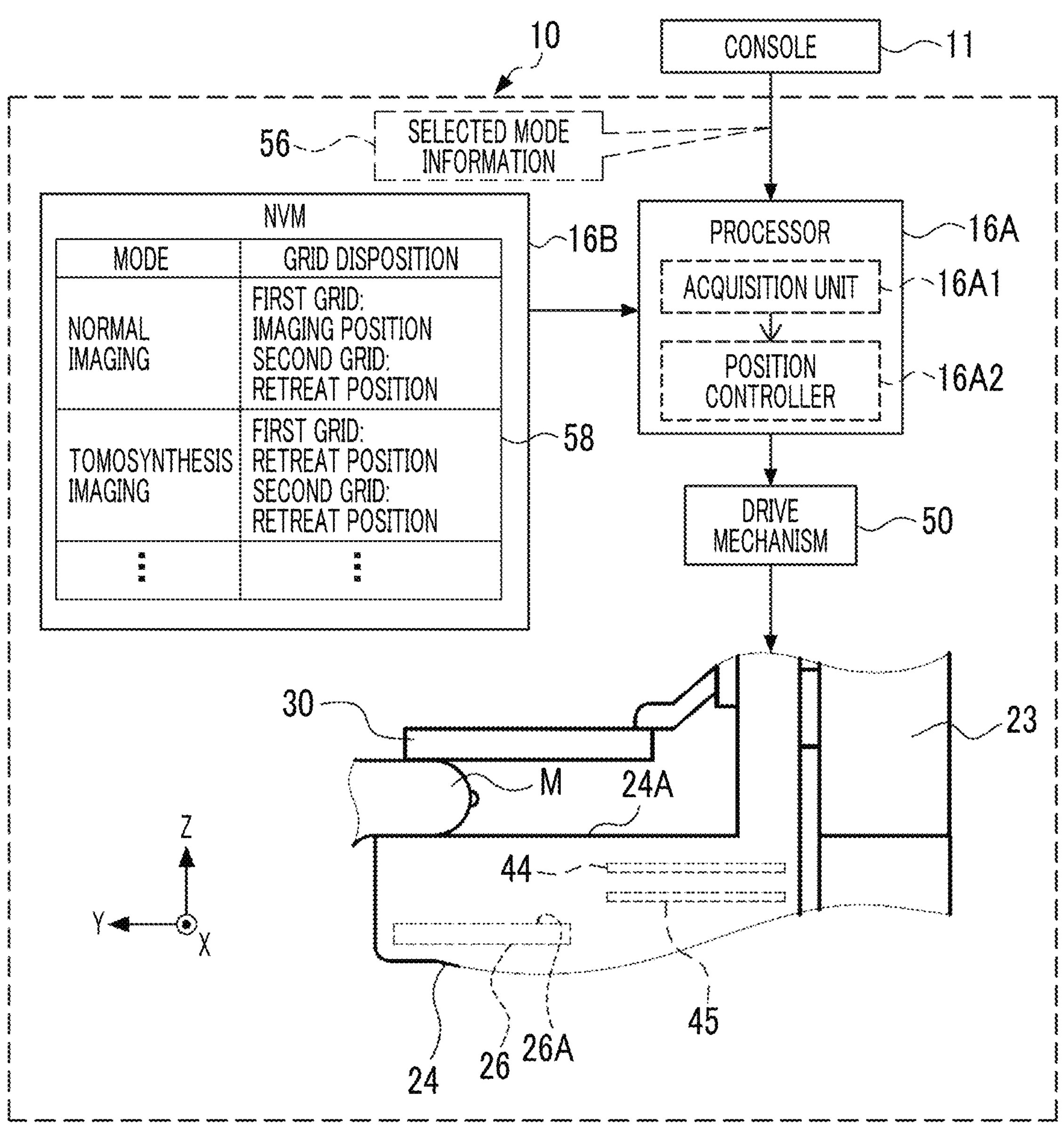
FIG. 14 is a conceptual diagram showing an example of the function of the mammography apparatus.

As an example, as shown in FIG. 14, the imaging mode selection of the user is received in the console 11. Here, the tomosynthesis imaging is selected. The console 11 outputs the selected mode information 56 to the mammography apparatus 10. That is, the console 11 outputs the result of receiving the imaging mode selection of the user.

In the processor 16A, the acquisition unit 16A1 acquires the selected mode information 56 from the console 11. In addition, the acquisition unit 16A1 acquires a grid position table 58 from the NVM 16B. The position controller 16A2 derives the grid disposition according to the imaging mode indicated by the selected mode information 56 by using the grid position table 58. Then, the position controller 16A2 controls the drive mechanism 50 such that the derived grid disposition is realized.

In the example shown in FIG. 14, since the tomosynthesis imaging mode is selected by the user, the first grid 44 and the second grid 45 are disposed at the retreat position. In the tomosynthesis imaging, as compared with the normal imaging or the contrast energy subtraction imaging, in a case in which the imaging is performed without using the scattered ray removal grid, a dose reaching the radiation detector 26 is increased, so that the image quality of the radiation image is improved. In addition, in the tomosynthesis imaging, the influence of the decrease in contrast due to the scattered rays is also smaller than the influence in the normal imaging or the contrast energy subtraction imaging. Therefore, in the tomosynthesis imaging, the imaging is performed in a state in which the first grid 44 and the second grid 45 are disposed at the retreat position. As described above, the position controller 16A2 executes the control of the disposition states of the first grid 44 and the second grid 45 inside the imaging table 24 according to the imaging mode selection of the user.

In FIG. 15, imaging modes and the grids used in the mammography apparatus 10 according to the present embodiment are summarized. As shown in FIG. 15, in the normal imaging, the first grid 44 is used. In the first grid 44, the boundary line 48 extends along the front-rear direction. In the grid disposition, the first grid 44 is disposed at the imaging position, and the second grid 45 is disposed at the retreat position.

In addition, in a case of the contrast energy subtraction imaging for diagnosis (that is, energy subtraction imaging for diagnosis), the first grid 44 is used. In the first grid 44, the boundary line 48 extends along the front-rear direction. In the disposition state of the grid, the first grid 44 is disposed at the imaging position, and the second grid 45 is disposed at the retreat position.

In addition, in a case of the contrast energy subtraction imaging for biopsy (that is, energy subtraction imaging for biopsy), the second grid 45 is used. In the second grid 45, the boundary line 48 extends in the left-right direction (that is, the movement direction of the tube 25A). In the disposition state of the grid, the first grid 44 is disposed at the retreat position, and the second grid 45 is disposed at the imaging position.

In a case of the tomosynthesis imaging, neither the first grid 44 nor the second grid 45 is used. In the disposition state of the grid, both the first grid 44 and the second grid 45 are disposed at the retreat position. In this way, the disposition state of the grid is changed according to the imaging mode selected by the user.

As described above, in the mammography apparatus 10 according to the present embodiment, the first grid 44 and the second grid 45 are provided inside the imaging table 24 as the scattered ray removal grids. The first grid 44 and the second grid 45 can be switched between the imaging position and the retreat position according to the imaging of each of the plurality of imaging modes. Then, in the control device 16 of the mammography apparatus 10, the acquisition unit 16A1 of the processor 16A acquires the result of receiving the imaging mode selection of the user. In addition, the position controller 16A2 executes the control of the disposition states of the first grid 44 and the second grid 45 inside the imaging table 24 according to the imaging mode selection acquired by the acquisition unit 16A1. As a result, even in the mammography apparatus 10 in which the scattered ray removal grids of different types are built inside the imaging table 24, it is possible to realize the disposition of an appropriate scattered ray removal grid according to the imaging mode selected by the user.

In addition, for example, since the first grid 44 and the second grid 45 can be disposed inside the imaging table 24, the scattered ray removal grids can be disposed near the detection surface 26A of the radiation detector 26 as compared with a case in which the scattered ray removal grids are disposed outside the imaging table 24, and thus the scattered ray removal effect is improved.

In addition, in the mammography apparatus 10 according to the present embodiment, in the scattered ray removal grid, the plurality of transmission parts 47 and the plurality of absorption parts 46 are alternately arranged, and the boundary line 48 between the transmission part 47 and the absorption part 46 extends in one direction. The direction in which the boundary line 48 extends in the first grid 44 and the direction in which the boundary line 48 extends in the second grid 45 intersect with each other. As a result, even in a case in which the directions of the boundary lines 48 of the first grid 44 and the second grid 45 are different from each other, an appropriate scattered ray removal grid can be disposed according to the imaging mode selected by the user.

In addition, in the mammography apparatus 10 according to the present embodiment, the direction in which the boundary line 48 extends the first grid 44 is parallel to the front-rear direction, and the direction in which the boundary line 48 extends in the second grid 45 is parallel to the left-right direction. As a result, even in a case in which the directions of the boundary lines 48 of the first grid 44 and the second grid 45 are orthogonal to each other, an appropriate scattered ray removal grid can be disposed according to the imaging mode selected by the user.

In addition, in the mammography apparatus 10 according to the present embodiment, the plurality of imaging modes include the normal imaging mode in which the imaging is performed by holding the radiation source 25 at a position facing the imaging table 24 in the vertical direction. Then, in a case in which the normal imaging mode is selected, the first grid 44 is disposed at the imaging position, and the second grid 45 is disposed at the retreat position. In a case of the normal imaging, the scattered ray removal grid is swung while the radiation source 25 is held at a position facing the imaging table 24. Therefore, the first grid 44 in which the direction of the boundary line 48 is the front-rear direction (that is, the depth direction of the imaging table) is used, whereas the second grid 45 in which the direction of the boundary line 48 is the left-right direction is retracted. As a result, an appropriate scattered ray removal grid according to the imaging mode selected by the user can be disposed.

In addition, in the mammography apparatus 10 according to the present embodiment, the plurality of imaging modes include the imaging mode via the contrast energy subtraction imaging for diagnosis (that is, the energy subtraction imaging mode for diagnosis). Then, in a case in which the energy subtraction imaging mode for diagnosis is selected, the first grid 44 is disposed at the imaging position, and the second grid 45 is disposed at the retreat position. In a case of the energy subtraction imaging for diagnosis, the scattered ray removal grid is swung while the radiation source 25 is held at a position facing the imaging table 24. Therefore, the first grid 44 in which the direction of the boundary line 48 is the front-rear direction (that is, the depth direction of the imaging table 24) is used, whereas the second grid 45 in which the direction of the boundary line 48 is the left-right direction is retracted. As a result, an appropriate scattered ray removal grid according to the imaging mode selected by the user can be disposed.

In addition, in the mammography apparatus 10 according to the present embodiment, the plurality of imaging modes include the imaging mode via the contrast energy subtraction imaging for biopsy (that is, the energy subtraction imaging mode for biopsy). Then, in a case in which the energy subtraction imaging mode for biopsy is selected, the second grid 45 is disposed at the imaging position, and the first grid 44 is disposed at the retreat position. In the biopsy, in order to sample the lesion, the lesion is three-dimensionally imaged by moving the radiation source 25 and performing the stereo imaging to confirm the position of the lesion in the breast M. In this case, the second grid 45 is stationary. Therefore, in a case of the energy subtraction imaging for biopsy, the second grid 45 in which the direction of the boundary line 48 is the left-right direction is used. On the other hand, the first grid 44 in which the direction of the boundary line 48 is the front-rear direction is retracted. As a result, an appropriate scattered ray removal grid according to the imaging mode selected by the user can be disposed.

The second grid 45 is a scattered ray removal grid suitable for the stereo imaging. That is, in a case in which the biopsy is performed, there is a case in which the stereo imaging is performed to three-dimensionally understand the position of the tissue that is the biopsy target in the breast M. In the stereo imaging, an irradiation position of the radiation R is changed in the left-right direction, so that the irradiation angle of the radiation R is changed and the imaging is performed a plurality of times. In the present configuration, the second grid 45 can be disposed in a posture in which a direction in which the boundary line 48 between the absorption part 46 and the transmission part 47 of the second grid 45 extends is parallel to the left-right direction. For this reason, as compared with a case in which the second grid 45 is disposed in a posture in which the extending direction of the boundary line 48 is parallel to the front-rear direction, it is possible to suppress vignetting of the effective radiation R (radiation other than the scattered rays) that is obliquely incident from the tube 25A toward the imaging surface 24A. This is because, in a case in which the second grid 45 is disposed in the posture in which the extending direction of the boundary line 48 is parallel to the front-rear direction, the absorption part 46 that extends in parallel to the boundary line 48 and the central axis of the flux of the radiation R connecting the focal point of the tube 25A and the imaging surface 24A intersect with each other. That is, since the movement direction of the tube 25A and the extending direction of the absorption part 46 are orthogonal to each other, vignetting by the absorption part 46 occurs with respect to the radiation R emitted from the tube 25A.

Further, in a case of the biopsy, in order to acquire a breast image in which the biopsy target in which the new blood vessels are dense is emphasized, in some cases, the imaging in which the stereo imaging and the contrast energy subtraction imaging are combined is performed. The present configuration is particularly effective in such a case. This is because, in the contrast energy subtraction imaging, a difference between two images captured with the radiation having different energies is obtained, so that the contrast is likely to be decreased. In the present configuration, the incidence of the scattered rays is suppressed by using the second grid 45, so that the decrease in the contrast can be suppressed. It should be noted that, as a method of suppressing the decrease in the contrast, it is also conceivable to increase a gain of a signal output by the radiation detector 26 in image correction processing. However, since the noise is also increased in a case in which the gain is increased, the method using the second grid 45 is preferable.

In the mammography apparatus 10 according to the present embodiment, the plurality of imaging modes include the tomosynthesis imaging mode in which the tomosynthesis of the breast M is performed while moving the radiation source 25. Then, in a case in which the tomosynthesis imaging mode is selected, both the first grid 44 and the second grid 45 are disposed at the retreat position. In the tomosynthesis imaging, the scattered ray removal grid is not used because the influence of scattered rays on the imaging result is small as compared with other imaging methods. Therefore, the first grid 44 and the second grid 45 are disposed at the retreat position. As a result, an appropriate scattered ray removal grid according to the imaging mode selected by the user can be disposed.

In the mammography apparatus 10 according to the present embodiment, inside the imaging table 24, the movement of the first grid 44 and the second grid 45 between the imaging position and the retreat position is the linear movement. The configuration in which the movement of the scattered ray removal grid inside the imaging table 24 is the linear movement contributes to the size reduction of the imaging table 24 as compared with a case of the rotational movement. In particular, in a case in which the direction of the linear movement is the front-rear direction, the space in the depth direction of the imaging table 24 can be effectively used.

In addition, in the mammography apparatus 10 according to the present embodiment, the processor 16A of the control device 16 causes the output unit 16A3 to output the disposition states of the first grid 44 and the second grid 45 inside the imaging table 24 to the display 11B1. The disposition states of the first grid 44 and the second grid 45 are displayed on the screen of the display 11B1. The user can confirm the disposition states of the first grid 44 and the second grid 45 inside the imaging table 24 by viewing the screen of the display 11B1. As a result, it is easy for the user to understand the disposition of the scattered ray removal grid inside the imaging table 24.

Modification Example

In the mammography apparatus 10 according to the embodiment described above, the form example is described in which one imaging mode of the plurality of imaging modes is executed, but the technology of the present disclosure is not limited thereto. In the present modification example, the imaging mode includes a continuous imaging mode in which two or more imaging modes of the plurality of imaging modes are continuously performed.

Figure 16:
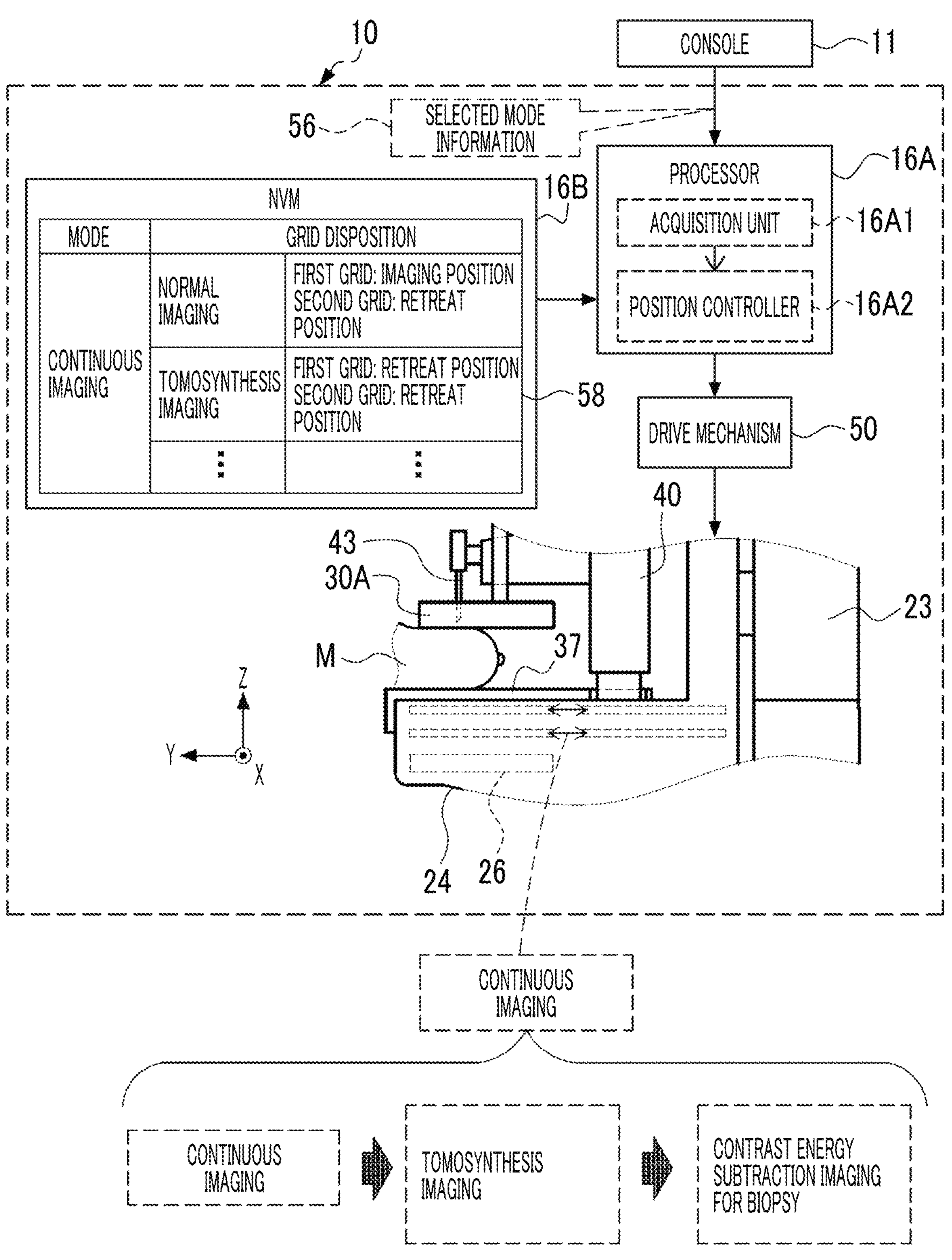
FIG. 16 is a conceptual diagram showing an example of the function of the mammography apparatus.

As an example, as shown in FIG. 16, the imaging mode selection of the user is received in the console 11. Here, the continuous imaging is selected. As an example of the continuous imaging, the normal imaging, the tomosynthesis imaging, and the energy subtraction imaging for biopsy are continuously performed in this order. The console 11 outputs the selected mode information 56 to the mammography apparatus 10. That is, the console 11 outputs the result of receiving the imaging mode selection of the user.

In the processor 16A, the acquisition unit 16A1 acquires the selected mode information 56 from the console 11. In addition, the acquisition unit 16A1 acquires a grid position table 58 from the NVM 16B. The position controller 16A2 derives the grid disposition according to the imaging mode indicated by the selected mode information 56 by using the grid position table 58. Here, the grid disposition in a case of the normal imaging and the grid disposition in a case of the tomosynthesis imaging are shown in the grid position table 58. Then, the position controller 16A2 controls the drive mechanism 50 such that the derived grid disposition is realized according to each imaging mode in the continuous imaging.

In the example shown in FIG. 16, the continuous imaging mode is selected by the user. First, the grid disposition according to the normal imaging mode is executed. That is, the first grid 44 is disposed at the imaging position, and the second grid 45 is disposed at the retreat position. After the imaging of the breast M in the normal imaging mode is performed, the grid disposition according to the tomosynthesis imaging mode is executed. That is, the first grid 44 and the second grid 45 are disposed at the retreat position. Then, after the breast M is imaged in the tomosynthesis imaging mode, the grid disposition according to the energy subtraction imaging mode for biopsy is performed. That is, the first grid 44 is disposed at the retreat position, and the second grid 45 is disposed at the imaging position. As described above, the position controller 16A2 executes the control of the disposition states of the first grid 44 and the second grid 45 inside the imaging table 24 in each imaging mode of the continuous imaging mode. That is, the disposition states of the first grid 44 and the second grid 45 are changed according to each imaging mode of the continuous imaging mode.

In addition, in the continuous imaging mode, the imaging in each mode in the continuous imaging mode can be executed in a state in which the breast M is being compressed between the imaging table 24 and the compression plate 30A. Stated another way, the imaging is performed during the continuous imaging mode without changing a compression height (that is, the height of the compression plate 30A with respect to the imaging table 24). In the example shown in FIG. 16, the normal imaging, the tomosynthesis imaging, and the energy subtraction imaging for biopsy are continuously executed in a state in which the breast M is being compressed.

As described above, in the mammography apparatus 10 according to the present modification example, the imaging mode includes the continuous imaging mode. The continuous imaging mode is an imaging mode in which, for example, the normal imaging, the tomosynthesis imaging, and the energy subtraction imaging for biopsy are executed in this order. Then, the position controller 16A2 executes the control of the disposition states of the first grid 44 and the second grid 45 according to each imaging mode of the continuous imaging mode. That is, in the continuous imaging mode in which the plurality of imaging modes are combined, the disposition states of the first grid 44 and the second grid 45 are controlled according to each mode. As a result, even in the continuous imaging mode, an appropriate scattered ray removal grid according to the imaging mode selected by the user can be disposed.

For example, after the imaging in a certain imaging mode is executed, in a case in which the user selects the imaging in another imaging mode, the imaging mode needs to be selected each time. In the present configuration, in a case in which the continuous imaging mode is selected, the imaging in the plurality of imaging modes is continuously executed, so that the user's workload (for example, the workload of selecting the mode and the workload of the confirmation operation) is reduced.

In addition, in the mammography apparatus 10 according to the present modification example, in the continuous imaging mode, the imaging in each imaging mode in the continuous imaging mode can be executed in a state in which the breast M is being compressed by the compression plate 30A. Therefore, without changing the compression condition of the breast M, the imaging is executed in each imaging mode in the continuous imaging mode under the same condition. As a result, even in a case in which the imaging is performed in different imaging modes, the compression conditions are the same, and thus the work of comparing the radiation images or the like is facilitated.

It should be noted that, in the modification example described above, the form example is described in which the normal imaging, the tomosynthesis imaging, and the energy subtraction imaging for biopsy are continuously executed in this order as the continuous imaging mode, but the technology of the present disclosure is not limited to this. For example, as the continuous imaging mode, any two or more of the normal imaging, the tomosynthesis imaging, the energy subtraction imaging for diagnosis, or the energy subtraction imaging for biopsy may be combined. In the continuous imaging mode, the order in which each imaging mode is executed is not particularly limited.

In the embodiment described above, the form example is described in which the disposition state of the physical scattered ray removal grids are controlled, but the technology of the present disclosure is not limited to this. For example, an imaging method (so-called virtual grid) in which the influence of the scattered rays is removed by image processing without using the physical scattered ray removal grids (for example, the first grid 44 and the second grid 45) may be selectable. In this case, as a method of removing the scattered rays, the technology described in JP6006193B can be adopted.

In the embodiment described above, the form example is described in which the movement direction of the radiation source 25 is the left-right direction, but the technology of the present disclosure is not limited to this. In this case, the boundary line 48 of the second grid 45 extends along the movement direction of the radiation source 25 (direction other than the left-right direction), and the boundary line 48 of the first grid 44 extends in the direction orthogonal to the boundary line 48 of the second grid 45.

In the embodiment described above, the form example is described in which the boundary lines 48 of the first grid 44 and the second grid 45 are orthogonal to each other, but the technology of the present disclosure is not limited to this. For example, the boundary lines 48 of the first grid 44 and the second grid 45 may intersect with each other in an aspect other than the orthogonal aspect.

In the embodiment described above, the form example is described in which the first grid 44 and the second grid 45 have different directions of the boundary line 48, but the technology of the present disclosure is not limited to this. For example, the grid density may be different between the first grid 44 and the second grid 45.

In the embodiment described above, the form example is described in which the two scattered ray removal grids, that is, the first grid 44 and the second grid 45, are provided inside the imaging table 24, but the technology of the present disclosure is not limited thereto. For example, three or more scattered ray removal grids may be provided inside the imaging table 24.

In the embodiment described above, the form example is described in which the console 11 is a separate body from the mammography apparatus 10, but the technology of the present disclosure is not limited thereto. For example, the console 11 may be integrated with the mammography apparatus 10.

It should be noted that, in the embodiment described above, the form example is described in which the imaging in which the stereo imaging and the contrast energy subtraction imaging are combined is performed, but the technology of the present disclosure is not limited to this. For example, a form may be adopted in which only the stereo imaging is performed.

In addition, in the embodiment described above, the form example is described in which the stereo imaging is performed by moving the radiation source 25 in the left-right direction, but the technology of the present disclosure is not limited to this. For example, the radiation source 25 may be a so-called multi-source that comprises a plurality of tubes arranged along the left-right direction and emits the radiation R from each tube. In the multi-source, the plurality of tubes are arranged in the left-right direction, so that the stereo imaging can be performed, for example, by using the tubes at both ends in the left-right direction.

The described contents and the shown contents are the detailed description of the parts according to the technology of the present disclosure, and are merely examples of the technology of the present disclosure. For example, the description of the configuration, the function, the action, and the effect are the description of examples of the configuration, the function, the action, and the effect of the parts according to the technology of the present disclosure. Accordingly, it is needless to say that unnecessary parts may be deleted, new elements may be added, or replacements may be made with respect to the described contents and the shown contents within a range that does not deviate from the gist of the technology of the present disclosure. In addition, in order to avoid complications and facilitate understanding of the parts according to the technology of the present disclosure, the description of common technical knowledge or the like, which does not particularly require the description for enabling the implementation of the technology of the present disclosure, is omitted in the described contents and the shown contents.

All documents, patent applications, and technical standards described in the present specification are incorporated into the present specification by reference to the same extent as in a case in which the individual documents, patent applications, and technical standards are specifically and individually stated to be described by reference.

Regarding the embodiment described above, the following additional notes are further disclosed.

Additional Note 1

A mammography apparatus comprising: an imaging table on which a breast of a subject is placed and in which a detector that detects radiation transmitted through the breast is housed; and a processor, in which a first grid and a second grid that are scattered ray removal grids, which are able to remove scattered rays generated by the radiation scattering in the breast, and that are switchable between an imaging position and a retreat position according to imaging in each of a plurality of imaging modes are provided inside the imaging table, and the processor is configured to acquire a result of receiving imaging mode selection of a user, and execute control of disposition states of the first grid and the second grid inside the imaging table according to the acquired imaging mode selection.

Additional Note 2

The mammography apparatus according to additional note 1, in which, in the scattered ray removal grid, a plurality of transmission parts that transmit the radiation and a plurality of absorption parts that absorb the radiation are alternately arranged, and a boundary line between the transmission part and the absorption part extends in one direction, and a direction in which the boundary line extends in the first grid and a direction in which the boundary line extends in the second grid intersect with each other.

Additional Note 3

The mammography apparatus according to additional note 2, in which, in the imaging table, in a case in which a direction connecting a chest wall side on which a chest wall of the subject is located and a side opposite to the chest wall is defined as a front-rear direction, and a direction orthogonal to the front-rear direction is defined as a left-right direction, the direction in which the boundary line extends in the first grid is parallel to the front-rear direction, and the direction in which the boundary line extends in the second grid is parallel to the left-right direction.

Additional Note 4

The mammography apparatus according to any one of additional notes 1 to 3, in which the plurality of imaging modes include a normal imaging mode in which the imaging is performed by holding a radiation source at a position facing the imaging table, and in a case in which the normal imaging mode is selected, the first grid is disposed at the imaging position, and the second grid is disposed at the retreat position.

Additional Note 5

The mammography apparatus according to any one of additional notes 1 to 3, in which the plurality of imaging modes include a first contrast imaging mode that is an imaging mode for diagnosis via contrast energy subtraction, and in a case in which the first contrast imaging mode is selected, the first grid is disposed at the imaging position, and the second grid is disposed at the retreat position.

Additional Note 6

The mammography apparatus according to any one of additional notes 1 to 3, in which the plurality of imaging modes include a second contrast imaging mode that is an imaging mode for biopsy via contrast energy subtraction, and in a case in which the second contrast imaging mode is selected, the second grid is disposed at the imaging position, and the first grid is disposed at the retreat position.

Additional Note 7

The mammography apparatus according to any one of additional notes 1 to 3, in which the plurality of imaging modes include a tomosynthesis imaging mode in which tomosynthesis of the breast is performed by moving a radiation source, and in a case in which the tomosynthesis imaging mode is selected, both the first grid and the second grid are disposed at the retreat position.

Additional Note 8

The mammography apparatus according to additional notes 4, 6, and 7, in which the plurality of imaging modes include a continuous imaging mode in which at least any two of the normal imaging mode, the second contrast imaging mode, or the tomosynthesis imaging mode are continuously performed regardless of an order, and in the continuous imaging mode, the disposition states of the first grid and the second grid are changed according to each of the normal imaging mode, the second contrast imaging mode, and the tomosynthesis imaging mode.

Additional Note 9

The mammography apparatus according to additional note 8, in which, in the continuous imaging mode, the imaging in each mode in the continuous imaging mode is executable in a state in which the breast is being compressed between the imaging table and a compression plate.

Additional Note 10

The mammography apparatus according to any one of additional notes 1 to 9, in which, inside the imaging table, movement of the first grid and the second grid between the imaging position and the retreat position is linear movement.

Additional Note 11

The mammography apparatus according to any one of additional notes 1 to 10, in which the processor is configured to output the disposition states of the first grid and the second grid inside the imaging table to a notification unit.

What is claimed is:

1. A mammography apparatus comprising:
an imaging table configured to support placement of a breast of a subject, and to house a detector that detects radiation transmitted through the breast; and
a processor,
wherein a first grid and a second grid that are scattered ray removal grids, which are able to remove scattered rays generated by the radiation scattering in the breast, and that are switchable between an imaging position and a retreat position according to imaging in each of a plurality of imaging modes are provided inside the imaging table, and
the processor is configured to
acquire a result of receiving selection of an imaging mode from among the plurality of imaging modes by a user, and
execute control for moving the first grid and the second grid between the imaging position and the retreat position inside the imaging table according to the acquired selection of the imaging mode.

2. The mammography apparatus according to claim 1,
wherein, in the scattered ray removal grid, a plurality of transmission parts that transmit the radiation and a plurality of absorption parts that absorb the radiation are alternately arranged, and a boundary line between the transmission part and the absorption part extends in one direction, and
a direction in which the boundary line extends in the first grid and a direction in which the boundary line extends in the second grid intersect with each other.

3. The mammography apparatus according to claim 2,
wherein, in the imaging table, in a case in which a direction connecting a chest wall side on which a chest wall of the subject is located and a side opposite to the chest wall is defined as a front-rear direction, and a direction orthogonal to the front-rear direction is defined as a left-right direction,
the direction in which the boundary line extends in the first grid is parallel to the front-rear direction, and
the direction in which the boundary line extends in the second grid is parallel to the left-right direction.

4. The mammography apparatus according to claim 3,
wherein upon selecting a normal imaging mode in which the imaging is performed by holding a radiation source at a position facing the imaging table from among the plurality of imaging modes, the processor is configured to move the first grid to the imaging position, and the second grid to the retreat position.

5. The mammography apparatus according to claim 4, wherein upon selecting a second contrast imaging mode that is an imaging mode for biopsy via contrast energy subtraction, from among the plurality of imaging modes, the processor is configured to move the second grid to the imaging position, and the first grid to the retreat position.

6. The mammography apparatus according to claim 5,
wherein upon selecting a tomosynthesis imaging mode in which tomosynthesis of the breast is performed by moving a radiation source, from among the plurality of imaging modes, the processor is configured to move both the first grid and the second grid to the retreat position.

7. The mammography apparatus according to claim 6,
wherein upon selecting a continuous imaging mode in which at least any two of the normal imaging mode, the second contrast imaging mode, or the tomosynthesis imaging mode are continuously performed regardless of an order, from among the plurality of imaging modes, the processor is configured to change the first grid and the second grid according to each of the normal imaging mode, the second contrast imaging mode, and the tomosynthesis imaging mode.

8. The mammography apparatus according to claim 7, wherein, in the continuous imaging mode, the processor is configured to execute the imaging in each mode in the continuous imaging mode in a state in which the breast is being compressed between the imaging table and a compression plate.

9. The mammography apparatus according to claim 3, wherein upon selecting a first contrast imaging mode that is an imaging mode for diagnosis via contrast energy subtraction, from among the plurality of imaging modes, the processor is configured to move the first grid to the imaging position, and the second grid to the retreat position.

10. The mammography apparatus according to claim 3, wherein upon selecting a second contrast imaging mode that is an imaging mode for biopsy via contrast energy subtraction, from among the plurality of imaging modes, the processor is configured to move the second grid to the imaging position, and the first grid to the retreat position.

11. The mammography apparatus according to claim 3, wherein upon selecting a tomosynthesis imaging mode in which tomosynthesis of the breast is performed by moving a radiation source, from among the plurality of imaging modes, the processor is configured to move both the first grid and the second grid to the retreat position.

12. The mammography apparatus according to claim 1, wherein, inside the imaging table, movement of the first grid and the second grid between the imaging position and the retreat position is linear movement.

13. The mammography apparatus according to claim 1, wherein the processor is configured to output the imaging position and retreat position of the first grid and the second grid inside the imaging table to a notification unit.

* * * * *